US011328620B2

United States Patent
Grant et al.

(10) Patent No.: US 11,328,620 B2
(45) Date of Patent: May 10, 2022

(54) SYSTEM AND METHOD FOR PHYSICAL ACTIVITY PERFORMANCE ANALYSIS

(71) Applicant: Motion Metrics Limited, London (GB)

(72) Inventors: James Bruce Alexander Grant, London (GB); Pruthvikar Reddy Mosali, Derby (GB)

(73) Assignee: Motion Metrics Limited, London (GB)

( * ) Notice: Subject to any disclaimer, the term of this patent is extended or adjusted under 35 U.S.C. 154(b) by 301 days.

(21) Appl. No.: 15/154,347

(22) Filed: May 13, 2016

(65) Prior Publication Data

US 2016/0335913 A1 Nov. 17, 2016

Related U.S. Application Data

(60) Provisional application No. 62/162,342, filed on May 15, 2015.

(51) Int. Cl.
*G09B 19/00* (2006.01)
*G01L 1/14* (2006.01)
(Continued)

(52) U.S. Cl.
CPC ............ *G09B 19/0038* (2013.01); *A43B 3/34* (2022.01); *A43B 5/0401* (2013.01); *A43B 5/0415* (2013.01); *A61B 5/1118* (2013.01); *A61B 5/6807* (2013.01); *B32B 5/26* (2013.01); *B32B 7/12* (2013.01); *B32B 15/14* (2013.01); *B32B 15/20* (2013.01); *G01L 1/14* (2013.01); *G01S 19/19* (2013.01); *G01S 19/49* (2013.01); *A63B 69/18* (2013.01); *B32B 2307/202* (2013.01); *B32B 2307/4023* (2013.01);
(Continued)

(58) Field of Classification Search
CPC . G09B 19/0038; A43B 3/0005; A43B 5/0401; A61B 5/1118; G01L 1/14; G01S 19/49
USPC .......................................................... 434/252
See application file for complete search history.

(56) References Cited

U.S. PATENT DOCUMENTS 4,906,192 A * 3/1990 Smithard .............. A63B 69/00
434/253
5,344,323 A * 9/1994 Burns .................... A63B 69/00
434/247
(Continued)

FOREIGN PATENT DOCUMENTS

| EP | 2657924 | 10/2013 |
|---|---|---|
| EP | 2657924 A1 | 10/2013 |
| WO | WO 2009/089406 | 7/2009 |

OTHER PUBLICATIONS

International Search Report for Application No. PCT/IB2016/000932, dated Mar. 1, 2017.
(Continued)

*Primary Examiner* — Thomas J Hong
*Assistant Examiner* — Sadaruz Zaman
(74) *Attorney, Agent, or Firm* — Intrinsic Law Corp.

(57) ABSTRACT

Systems, methods, and computer-readable storage media for improving physical activity performance analysis, and more specifically to a system and method for using motion, pressure and position sensors embedded in equipment or footwear of a user to assess physical activity performance. The sensors can collect pressure related data, transmit the data to a server for processing, and the user can receive feedback based on their performance.

22 Claims, 19 Drawing Sheets

(51) Int. Cl.

| | |
|---|---|
| *A43B 5/04* | (2006.01) |
| *A43B 3/00* | (2022.01) |
| *A61B 5/11* | (2006.01) |
| *A61B 5/00* | (2006.01) |
| *G01S 19/19* | (2010.01) |
| *G01S 19/49* | (2010.01) |
| *B32B 5/26* | (2006.01) |
| *B32B 7/12* | (2006.01) |
| *B32B 15/20* | (2006.01) |
| *B32B 15/14* | (2006.01) |
| *H04W 88/02* | (2009.01) |
| *A63B 69/18* | (2006.01) |
| *A43B 3/34* | (2022.01) |

(52) U.S. Cl.
CPC ..... *B32B 2307/546* (2013.01); *B32B 2437/02* (2013.01); *B32B 2457/08* (2013.01); *H04W 88/02* (2013.01)

(56) References Cited

U.S. PATENT DOCUMENTS

| | | | | | |
|---|---|---|---|---|---|
| 6,018,705 | A * | 1/2000 | Gaudet | ............... | A61B 5/1121 235/105 |
| 6,445,960 | B1 * | 9/2002 | Borta | ............... | G09B 9/02 434/30 |
| 6,539,336 | B1 * | 3/2003 | Vock | ............... | A42B 3/0433 702/178 |
| 8,736,439 | B1 | 5/2014 | Shinozuka | | |
| 2003/0009308 | A1 * | 1/2003 | Kirtley | ............... | G01P 1/127 702/141 |
| 2004/0219498 | A1 * | 11/2004 | Davidson | ............... | A63B 69/00 434/247 |
| 2005/0038626 | A1 * | 2/2005 | Flentov | ............... | A63C 11/00 702/141 |
| 2007/0006489 | A1 * | 1/2007 | Case, Jr. | ............... | A43B 5/06 36/132 |
| 2008/0214360 | A1 * | 9/2008 | Stirling | ............... | A61B 5/1118 482/9 |
| 2009/0048044 | A1 * | 2/2009 | Oleson | ............... | A63B 43/00 473/570 |
| 2009/0048070 | A1 * | 2/2009 | Vincent | ............... | A63B 71/0686 482/8 |
| 2009/0137933 | A1 | 5/2009 | Lieberman et al. | | |
| 2010/0063778 | A1 * | 3/2010 | Schrock | ............... | A61B 5/6807 702/188 |
| 2010/0152619 | A1 * | 6/2010 | Kalpaxis | ............... | A61B 5/1038 600/592 |
| 2012/0183940 | A1 * | 7/2012 | Aragones | ............... | A61B 5/744 434/247 |
| 2013/0041617 | A1 * | 2/2013 | Pease | ............... | A63B 71/0622 702/139 |
| 2013/0190903 | A1 * | 7/2013 | Balakrishnan | ............... | A63B 71/06 700/91 |
| 2015/0067811 | A1 * | 3/2015 | Agnew | ............... | H04L 67/06 726/9 |
| 2016/0335913 | A1 * | 11/2016 | Grant | ............... | B32B 5/26 |
| 2017/0087411 | A1 * | 3/2017 | Bender | ............... | A43B 5/04 |
| 2019/0076063 | A1 * | 3/2019 | Kent | ............... | A61B 5/1118 |
| 2019/0353902 | A1 * | 11/2019 | Zhovnirovsky | ............... | A61B 5/742 |

OTHER PUBLICATIONS

PCT Written Opinion of the International Searching Authority (ISA) for Application No. PCT/IB2016/000932, dated Apr. 2015.

Hoffmann, et al., "Road-Quality Classification and Bump Detection With Bicycle-Mounted Smartphones," UDM 13, Proceedings of the 3rd International Conference on Ubiquitous Data Mining,dated Mar. 1, 2013, 5 pages.

Information on Search Strategy for Application No. PCT/IB2016/000932, 1 page.

Communication Pursuant to Article 94(3) EPC dated Aug. 16, 2019 From the European Patent Office Re. Application No. 16766599.1. (8 Pages).

Communication Pursuant to Article 94(3) EPC dated Dec. 10, 2020 From the European Patent Office Re. Application No. 16766599.1. (12 Pages).

* cited by examiner

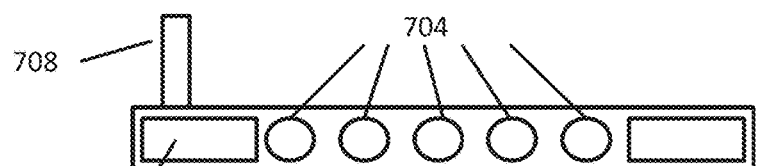
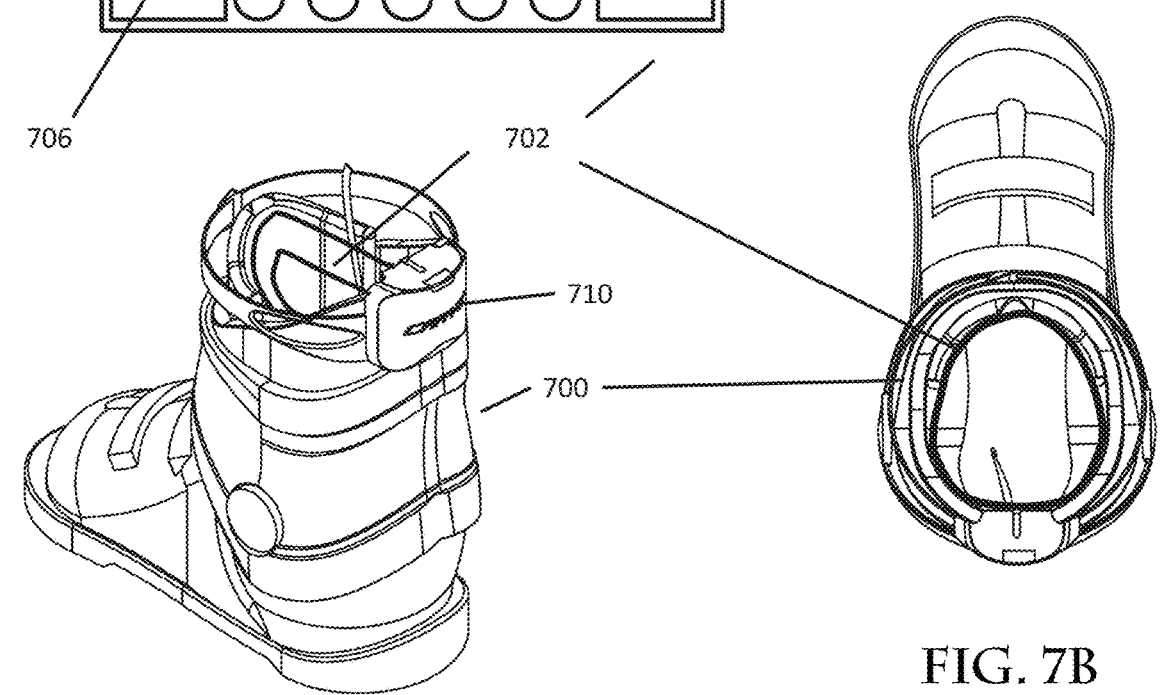
FIG. 7C
FIG. 7B
FIG. 7A

SYSTEM AND METHOD FOR PHYSICAL ACTIVITY PERFORMANCE ANALYSIS

PRIORITY

The present application claims priority to U.S. Provisional Application 62/162,342, filed May 15, 2015, the contents of which is incorporated herein by reference in its entirety.

BACKGROUND

Technical Field

The present disclosure generally relates to physical activity performance analysis, and more specifically to a system and method for using motion, pressure and position sensors embedded in equipment or footwear of a user to assess physical activity performance.

Introduction

An important component to learning new skills is feedback. Often, this feedback is provided by coaches or instructors. For example, a basketball player can employ a coach to give feedback for improving their shot or dribbling, or a weightlifter can record a video of their lifting process to improve their ability to move the bar. While such feedback systems can help athletes improve, they have drawbacks. For example, it is difficult for a skier relying on a coach to receive real-time feedback. Moreover, such methods of critiquing a performance often have subjective biases rather than relying on quantitative data.

BRIEF DESCRIPTION OF THE DRAWINGS

FIG. 7A contains an exposed view of a pressure sensing band and main unit sensor system design in accordance with a first exemplary embodiment;

FIG. 7B contains an exposed view of a pressure sensing band and main unit sensor system design in accordance with a second exemplary embodiment;

FIG. 7C illustrates and exemplary exposed view of the pressure sensing band;

DETAILED DESCRIPTION

Figure 1:
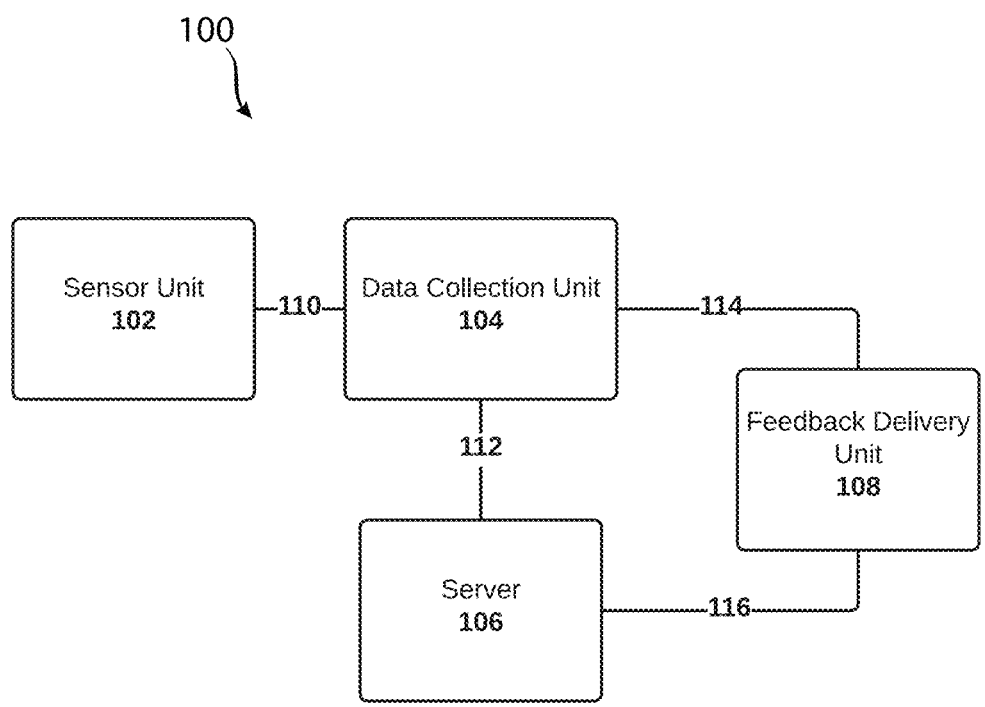
FIG. 1 is a block diagram illustrating components of a performance analysis system in accordance with an exemplary embodiment.

A system, method and computer-readable media are disclosed which aide in physical activity performance analysis, and more specifically to using motion, pressure and position sensors embedded in equipment or footwear of a user to assess physical activity performance. Various embodiments of the disclosure are described in detail below. While specific implementations are described, it should be understood that this is done for illustration purposes only. The description is not to be considered as limiting the scope of the embodiments described herein. Other components and configurations may be used without parting from the spirit and scope of the disclosure.

The term "coupled" is defined as connected, whether directly or indirectly through intervening components, and is not necessarily limited to physical connections. The term "substantially" is defined to be essentially conforming to the particular dimension, shape or other word that substantially modifies, such that the component need not be exact. For example, substantially rectangular means that the object in question resembles a rectangle, but can have one or more deviations from a true rectangle.

The phrase "physical activity" refers to sports (such as running, cycling, mountain biking, skating, skiing, snowboarding, tennis, squash, rowing, horse riding, soccer, rugby, surfing, kitesurfing, wakeboarding, water skiing, golf, or lacrosse) and non-sports activities (such as dance, walking, fashion runway walking). The phrase "activity performance" refers to the proficiency in the skill or technique used for the activity. For instance, activity performance for skiing could refer to the proficiency of the skier including aspects of technique such as the smoothness of turning, appropriate edge angle to the slope, balance of the skier, or ability to navigate types of terrain. To give another example, the activity performance in ballet would refer to movement and the accuracy of foot stretch, point, wing, lift arch, ankle, demi pointe or pointe. For fashion walking, activity performance could refer to the gait, stride length, speed of turn or synchronization of the model with others in a group. A "performance" can refer to both a "snapshot" of the user performing the activity (i.e., how the user is performing at a single point in time) or an entirety of an athletic performance (i.e., an entire ski run). The phrase "real-time" is according to the common vernacular of those persons skilled in this art—that is, a description for a system that responds to an external event within a short and predictable time frame (i.e., with immediacy).

The invention addresses the many difficulties associated with traditional instructor based physical activity and video analysis tuition; including, the expense of finding and paying an instructor, the limited resources of instructor for individuals when teaching a class, the outcome that people coach themselves without feedback and difficulties teaching a class of students with a dispersion of abilities. More specifically, the present disclosure relates to a system including motion, pressure and position sensors to collect data, process, and display data and analytics to augment and replace the current visual and verbal interactions of activity instructors with their pupils. The invention replicates the experience of an instructor by processing sensor data in novel methods to give real-time advice to the user, either through headphones or near eye displays; near-real time advice on a portable display, such as a mobile phone; or long term in-depth analysis either on a mobile phone, tablet or a computing device. By incorporating feedback from the system into their training, the user can improve their performance. The use of machine generated feedback has the advantage that it is objective and can be tailored to the specific activity, discipline, or style within a given activity.

Referring to FIG. 1, a block diagram overview in accordance with an exemplary embodiment is illustrated. The system 100 can include a Sensor Unit 102, a Data Collection Unit 104, a Server 106 and a Feedback Delivery Unit 108. The Sensor Unit 102 can measure data related to a user's technique. The Data Collection Unit 104 can store and process performance information. The Server 106 can process the data and store the data. The Server 106 functions can include, but is not limited to, storage of user data, performance analysis, performance ranking of users or hosting of web based performance analysis. The Feedback Delivery Unit 108 can provide the user with feedback to improve the user's technique. The system 100 can include a plurality of Sensor Units 102. The Sensor Unit(s) 102, the Data Collection Unit 104 and/or the Feedback Delivery Unit 108 can be contained in one or more units. For example, a system 100 can include a Sensor Unit 102 for each foot of the user and another Sensor Unit 102 located on the upper body of the user. The Sensor Unit on the upper body may consist of the GPS 308, Accelerometer 204, Gyroscope 208, and Magnetometer 206 in a mobile phone, or any combination thereof. In addition, the Sensor Unit 102 can have other sensor components as required for the particular activity being measured. It is also possible for one or a plurality of the Sensor Unit(s) to share the same housing as the Data Collection Unit. The Sensor Unit 102 gathers sensor data and then transmits the data to the Data Collection Unit 104. The Sensor Unit 102 can be communicatively coupled with the Data Collection Unit 104 wirelessly or via one and/or more wires 110. Alternatively, the Sensor Unit 102 can store data for later transmission via 110 allowing the Sensor Unit 102 to function independently of the Data Collection Unit 104 for an extended period of time. Wireless transmission can be done via Bluetooth, Wi-Fi, or any radio frequency. The Data Collection Unit 104 can be communicatively coupled with the Server 106. When coupled, the Data Collection Unit 104 can transmit gathered data and can receive data (including data relating to the performance of other users, local maps, weather forecasts). The Server 106 functions can include, but are not limited to, storage of user data, performance analysis, performance ranking of users or hosting of web based performance analysis. The Data Collection Unit 104 can be communicatively coupled with the Server 106 wirelessly and/or via one or more wires 112. The wireless transmission can be done via the internet, Wi-Fi, and/or Bluetooth and/or via a combination of wired (via one or more wires 112) and wireless data transmission. The Feedback Delivery Unit 108 is communicatively coupled with the Data Collection Unit 104 and the Server 106. The coupling can be done via wireless transmission and/or via one or more wires, 114, 116. Connections 114 and 116 can be Bluetooth, Internet based, Wi-Fi, wired, or any radio frequency connection. In one or more embodiments, the Data Collection Unit 104 and Feedback Delivery Unit 108 can be contained in the same housing. The Feedback Delivery Unit 108 can convey performance feedback to the user, either visually, using a display, haptic feedback, through audio via a speaker and/or headphones, and/or through a third party device such as a near eye display. The feedback delivery units can take the form of, but are not limited to, a near eye display, a mobile phone, a tablet, a Personal Computer, a haptic feedback unit on the upper body, a haptic feedback unit on the insoles, or a haptic feedback unit residing within the footwear of the user or residing in and/or on the Sensor Unit(s).

Figure 2:
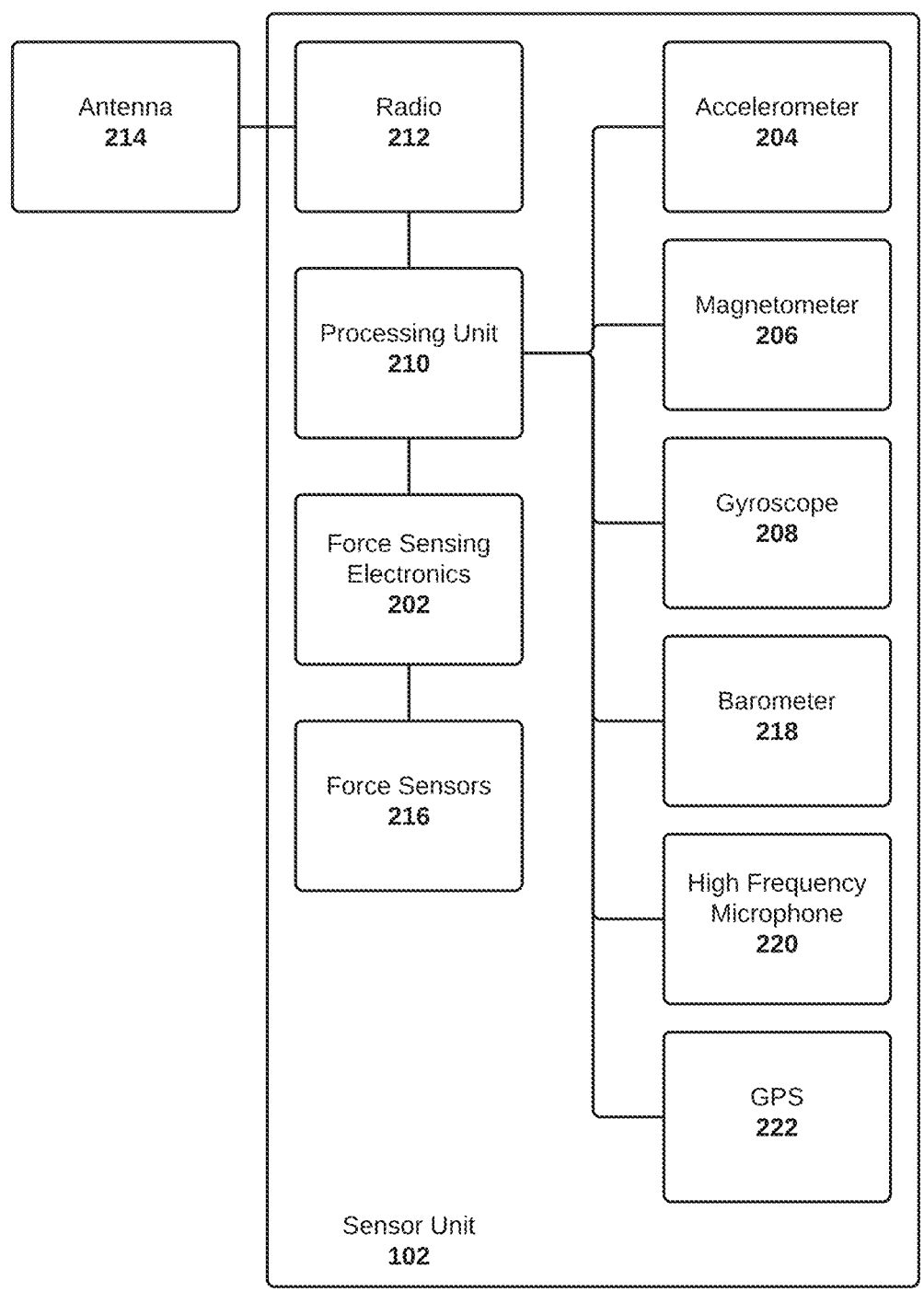
FIG. 2 is a block diagram of a Sensor Unit in accordance with an exemplary embodiment.

Referring to FIG. 2, a block diagram of the Sensor Unit in accordance with an exemplary embodiment is illustrated. The Sensor Unit 102 can be located on the body or equipment suitable for a given physical activity. For instance, for skiing the Sensor Unit 102 can be located in the ski boots, on the insole, and on or in the skis and/or bindings. For running, a Sensor Unit 102 can be placed in one or both of the shoes or insoles. For example, the sensor could be built into the shoe, placed below the insole, built into the insole, placed above the insole but below the foot, etc. For horse riding, a Sensor Unit 102 can be placed in one or both of the shoes or stirrups. The Sensor Unit 102 can include one or more sensors. For example, the sensors can include, but are not limited to, an Accelerometer 204, Magnetometer 206, Gyroscope 208, Global Positioning System (218), Microphone 220 and Force Sensors 216. The sensors can be internal sensors and/or external sensors. The Force Sensors 216 can be either capacitive or resistive sensors that are coupled to the Processing Unit 210 using Force Sensor Electronics 202. Data from the sensors is processed on the Processing Unit 210. The processed data can be sent to the Storage Unit 222 or the Radio Frequency Unit for transmission via the Antenna 214 by a wireless protocol such as Wi-Fi, Bluetooth or other Radio Frequency. The Force Sensor Electronics 202 can be coupled with the Force Sensors 216 to prepare force measurements for the Processing Unit 210. The Force Sensors 216 can include a capacitive sensing circuit with a digital output and/or a resistive circuit and one or more analog to digital converters. The Processing Unit 210 can provide several functions, including but not limited to; sensor fusion of data from the Accelerometer 204, Magnetometer 206 and Gyroscope 208, to calculate the orientation of the unit; the integration of orientation measurements and Accelerometer 204 measurement to provide dead-reckoning position estimates; the combination of GPS 308 with motion data; signal processing of sensors; and processing of data for compression in the Storage 302 or for transmission. Orientation can be computed in the processing unit 210 by combining the data from 204, 206 and 208 using a sensor fusion algorithm. Examples of possible sensor fusion algorithms that could be used include direct cosine matrix (See for instance, Premerlani, William, and Paul Bizard. "Direction cosine matrix IMU: Theory. "DIY DRONE: USA (2009): 13-15), an extended Kalman filter (See for instance, Marins, João Luís, et al. "An extended Kalman filter for quaternion-based orientation estimation using MARG sensors. "Intelligent Robots and Systems, 2001. Proceedings. 2001 IEEE/RSJ International Conference on. Vol. 4. IEEE, 2001) or other appropriate motion fusion algorithms. The Sensor Unit 100 can communicate with the Data Collection Unit 102 via the Antenna

214, where data is sent through the Processing Unit 210, to the Radio Frequency Unit 212 for transmission by the Antenna 214.

Figure 3:
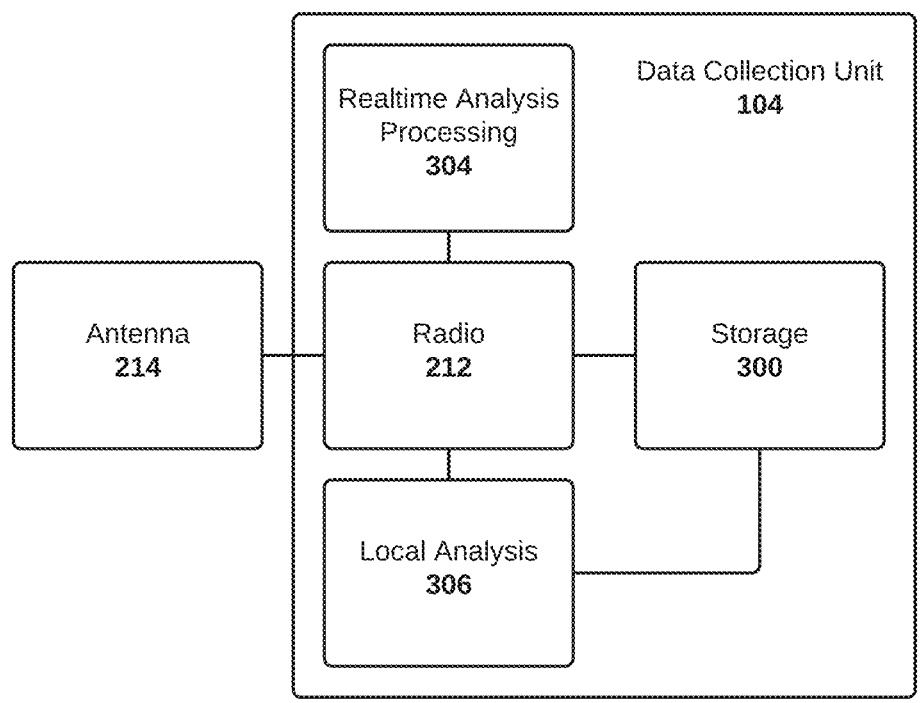
FIG. 3 is a block diagram of a Data Collection Unit in accordance with an exemplary embodiment.

Referring to FIG. 3, a block diagram of the Data Collection Unit in accordance with an exemplary embodiment is illustrated. The Data Collection Unit 104 can contain a Sensor Unit 102 and/or the Feedback Delivery Unit 108. Data from the Sensor Units 102 can be received through the antenna 214 by a wireless protocol such as Wi-Fi, Bluetooth or other radio frequencies. The data from the Radio unit 212 and the GPS Unit 308 can be sent to the Storage Unit 302 to generate a detailed user analysis 408 using the Local Analysis Unit 306 and later to a Website and Web Based Analysis 410. The data from 302 and the GPS Unit 308 can be sent to the Real-Time Analysis Processing Unit 304. The Real-Time Analysis Processing Unit 304 can calculate metrics to measure the performance of the activity of the user. The processed data can be sent to the Feedback Delivery Unit 108 either through the antenna 214 by a wireless protocol such as Wi-Fi, Bluetooth or other Radio Frequency or is embedded in the Data Collection Unit.

Figure 4:
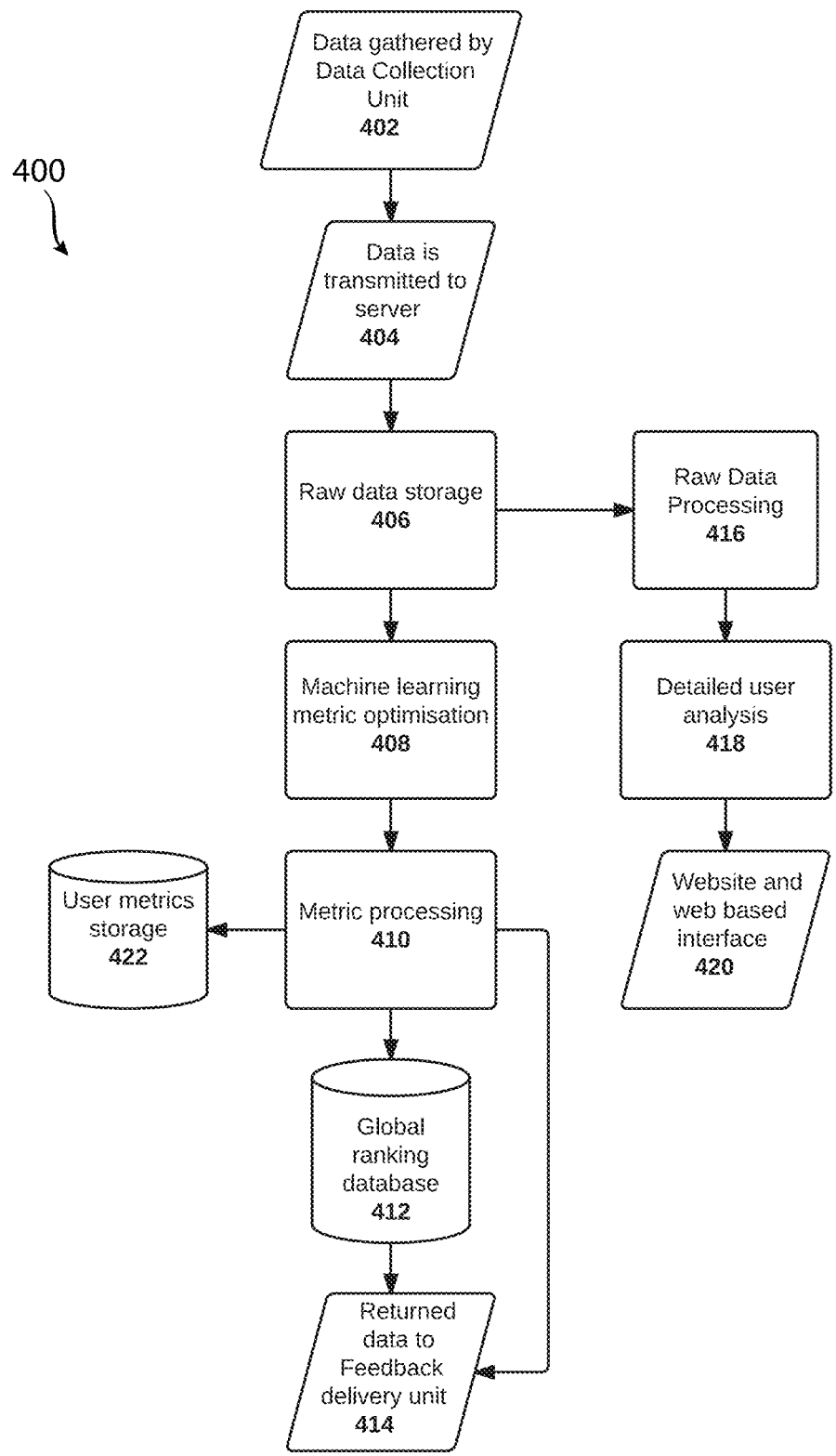
FIG. 4 is a flowchart for providing sensor information from a Data Collection Unit to the Server in accordance with an exemplary embodiment.

Referring to FIG. 4, a flowchart for a method for communicating data via a wide area network, in accordance with an exemplary embodiment is illustrated. The exemplary method 400 is provided by way of example, as there are a variety of ways to carry out the method. The method 400 described below can be carried out using the configurations illustrated in FIGS. 1-3 by way of example, and various elements of this figure are referenced in explaining exemplary method 400. Each block shown in FIG. 4 represents one or more processes, methods or subroutines, carried out in the exemplary method 400. The exemplary method 400 can begin at block 402.

At block 402, data is gathered. For example, the Data Collection Unit 104 gathers data from the Sensor Unit(s) 102. After gathering data, the method 400 proceeds to block 404. At block 404, data is transmitted to the server. For example, the Data Collection Unit 104 transmits data to the Server 106 using connection 108. After block 404 the method 400 proceeds to block 406. At block 406, the data is stored. For example, the data transmitted through the connection 108 is stored on Server 106. After block 406 the method 400 proceeds to block 408 and 416. At block 416 the data is processed. For example, the server 106 processes the data for the web based analysis platform. After block 416 method 400 proceeds to 418.

At block 418 the data is converted or transformed and stored. For example, the data is converted or transformed by the server 106 into a form suitable for in-depth web analysis and then stored. After block 418 the method 400 proceeds to block 420. At block 420 presents the data to allow for analysis. For example, the data is accessed on server 106 by external users for analysis of performance. At block 408 optimization for the machine learning algorithms takes place in the case where the provided data is from a user with a pre-classified (either manually or automatic) skill type. Example approaches could focus on choice of model parameters for metric calculation to distinguish between good and bad technique. Each performance metric is assigned a weighting then the users receive a weighted score. The metric weighting can be chosen so as to maximize the statistical significance of the difference between the groups of users with good and bad technique. For instance, in the case of a Weighted Least Squares classifier the introduced classified user data could be used to adjust metric weightings in order to maximize the squared sum of differences between the good and bad groups of users.

At block 410 metric processing is performed to calculate metrics related to the user's performance. The choice of metrics and their calculation is based on a model specific to the physical activity. For instance, in the case of skiing where sensor units are placed on each boot or ski of the skier as well as the body of the skier, performance metrics could include: (1) Transition point, defined as the point in the turn of the skier where the sum of the skier's center of mass (defined as the distance weighted sum of force measured by sensors) transfers from the left to the right foot (or right to the left). Where the point of turn for a given turn is defined, for instance, as the percentage of the whole turn that the skier turns through to complete the turn. For example, if the turn is 30 degrees (from furthest clockwise to furthest anti-clockwise direction) then 15 degrees through the turn corresponds to a 50 percent point (the transition point) of turn. The metric for transition point could be the average transition point across all of the turns (Average Across Turns) of the user or for a user's session. (2) Forward/back position, the percentage time that the skier's center of mass spends forward of a given threshold. (3) Left/right bias, the left/right distance the skiers time or distance averaged center of mass is away from the skier's center of mass when standing still. (4) The correlation coefficient between the time series forward/back center of mass and the speed of the skier. (5) The correlation coefficient between the forward/back center of mass and the steepness of the slope. (6) The percent of time or distance skied that the skis yaw of the skis pointing towards each other above a given threshold. (7) The correlation coefficient between the difference between the yaw of skis and the speed of the skier. (8) The correlation coefficient of the yaw difference between skis and the speed of the skier conditioned for when the skis are divergent (9) the percentage of time or distance skied that the skiers are diverging above a given threshold. (10) The correlation coefficient between the yaw difference of the skis and speed conditioned for when the skis are divergent. (11) The average of the maximum roll of the skis for turns. (12) The average difference in roll of the skis across turns. (13) The correlation coefficient between the maximum roll for the skis and the speed of the skier or steepness of the slope. (14) The correlation coefficient in the difference in roll of the skis and the speed of the skier or steepness of the slope. (15) The average speed of the skier. (16) The time of the skier for a given course. (17) The speed of the skier for given type of terrain. (18) The correlation coefficient for the yaw (or other angle) of the upper body and the sensors units on the skis. (19) The correlation coefficient between the yaw of the upper body and the lower body with a lead or lag relationship for a given time. After block 410 method 400 proceeds to block 412, 422 and 414.

At block 422 the user's performance metrics are stored. The user's performance metrics are stored in the storage unit 302.

At block 412 the metrics for a given user are compared against pre-classified groups of users to classify a given user by skill level of type of skill. For instance in the case of skiing, if there are two groups of skiers known as good and bad skiers then a simple Of Least Squares classifier would calculate the sum of squared metric differences between the good and the bad groups. The group that the given user has the lowest sum of squared metric difference is the group the user is classified as. It should be obvious to a person with ordinary skill in the art that similar machine learning approaches can be used such as Generalized Least Squares, Least Squares, Artificial Neural Network, Bayesian Statistics or Support Vector Machines, Expectation-maximization algorithm, Vector Quantization, Generative Topographic map, or Information Bottleneck method. The system then transmits the user ranking to the Feedback Delivery Unit 108. After block 412 method 400 proceeds to block 414.

Figure 5A:
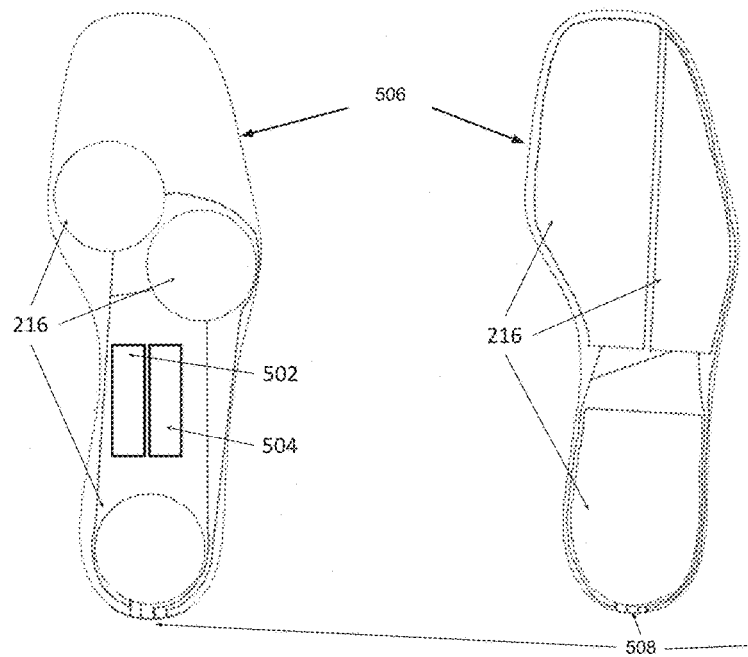
FIG. 5A contains an insole component for the Sensor Unit in accordance with a first exemplary embodiment.

Referring to FIG. 5A, an exposed view of an insole having the Force Sensors either wholly or partly embodying the Sensor Unit in accordance with an exemplary embodiment. As shown, the Force Sensors 216 are circular in form based on standard sensors available for manufacture. The battery unit 502 contained in (or on, or below) the insole 506 is used to power the system. The electronics unit 504 in the insole 506 wholly or partly contains the sensor unit 102. As shown, the insole 500a includes a first Force Sensor 216a, a second Force Sensor 216b and a third force sensor 216c.

Figure 5B:
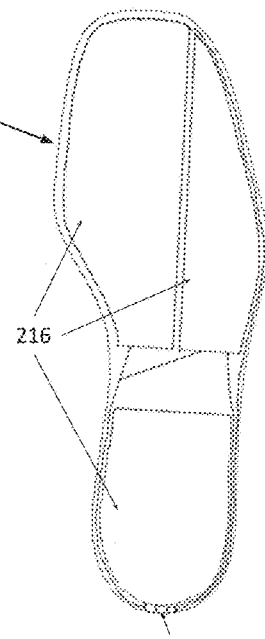
FIG. 5B contains an insole component for the Sensor Unit in accordance with a second exemplary embodiment.

Referring to FIG. 5B, an exposed view of the Force Sensors either wholly or partly embodying the Sensor Unit in accordance with an exemplary embodiment. The Sensor Unit 102 includes Force Sensors 216a, 216b and 216c of an organic shape that is form fitted to the foot. As shown, the insole 500b comprises three multi-component Force Sensors 216a, 216b, 216c of rectangular shapes.

Figure 5C:
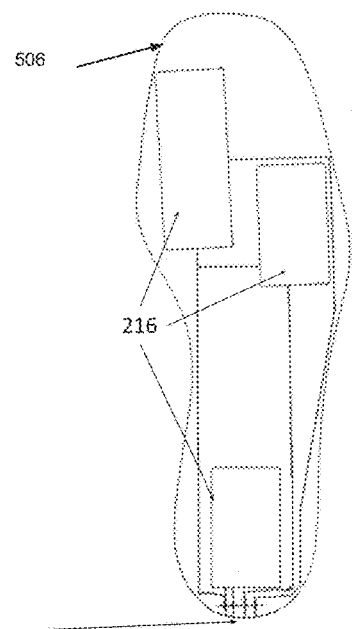
FIG. 5C contains an insole component for the Sensor Unit in accordance with a third exemplary embodiment.

Referring to FIG. 5C, an exposed view of an insole having circular Force Sensors embedded therein in (i.e., built into the insole itself) accordance with a third exemplary embodiment as illustrated. As shown, the insole 500c includes a first Force Sensor 216a, a second Force Sensor 216b and a third force sensor 216c.

Figure 6:
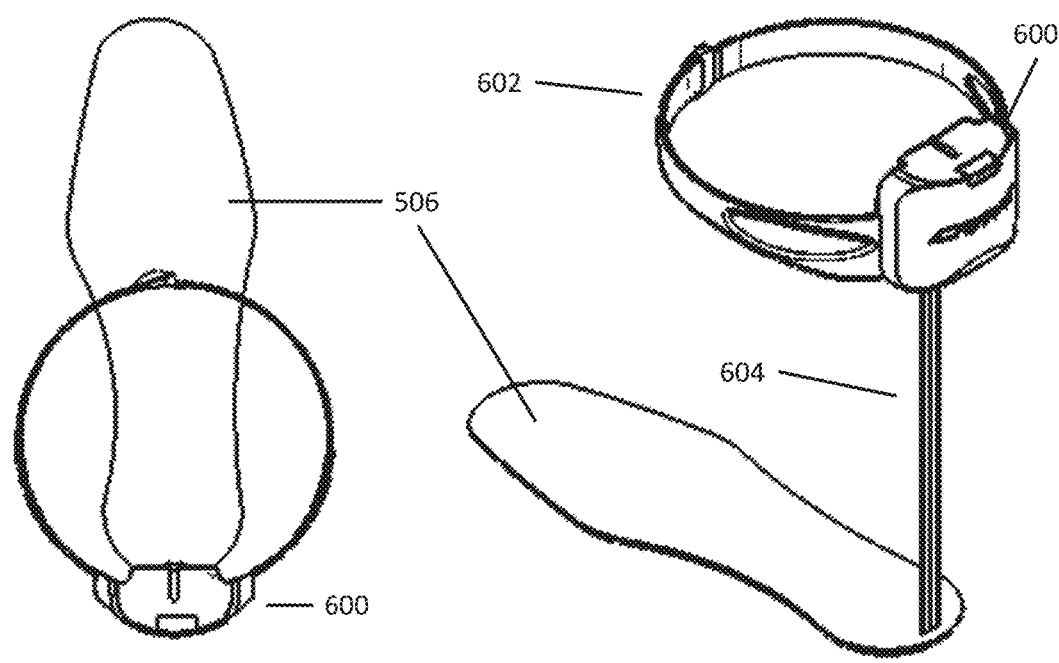
FIG. 6 is an overview of a separate insole main unit sensor system design of the Sensor Unit in accordance with an exemplary embodiment.

Referring to FIG. 6, an exposed view of an alternative design for the Sensor Unit. The depicted view is for the example implementation in a ski boot, but a similar design could be used for a variety of physical activities. The Sensor Unit 102 includes an Insole 506, a Main Housing 600, a Housing Strap 602 and one or more wires 604. The Sensor Unit 102 collects pressure data using Force Sensors 216 embedded in the Insole 506 which is transmitted through the one or more wires 604 to the Main Housing 600 for processing, storage and transmission. While in certain embodiments, the data collected can be actual pressure data, in other embodiments the pressure data can be pressure related data. Pressure related data can be data related to pressure, but obtained indirectly. For example, the Sensor Unit 102 can be configured to identify capacitance values which change based on how much pressure is being applied to the Sensor Unit 102. The capacitance values can have a linear or non-linear relationship to pressure, and therefore the data collected by the Sensor Unit 102 is "pressure related data." Using such data, estimations of pressure can be calculated. Although such estimations may or may not be directly tied to standard calculations of pressure, such estimations can be referred to as "pressure." The separation of the Insole 506 and Main Housing allows for an insole 506 with a preferred thickness range of 0.2-2 mm, but is not limited to this range, to avoid discomfort to the user. The one or more wires 604 can have a 0.1-0.5 mm thickness, but are not limited to this range, to ensure the user does not notice the one or more wires 604 in the boot. The wire can either run inside the inner part of the ski boot or be taken between the inner boot and outer boot. To ensure suitability for the cable, defined as a collection of wires encased in a housing material, to run inside the boot the cable can have a high friction on the side in contract with the boot compared with a lower friction on the side in contact with the leg of the user.

Figure 16:
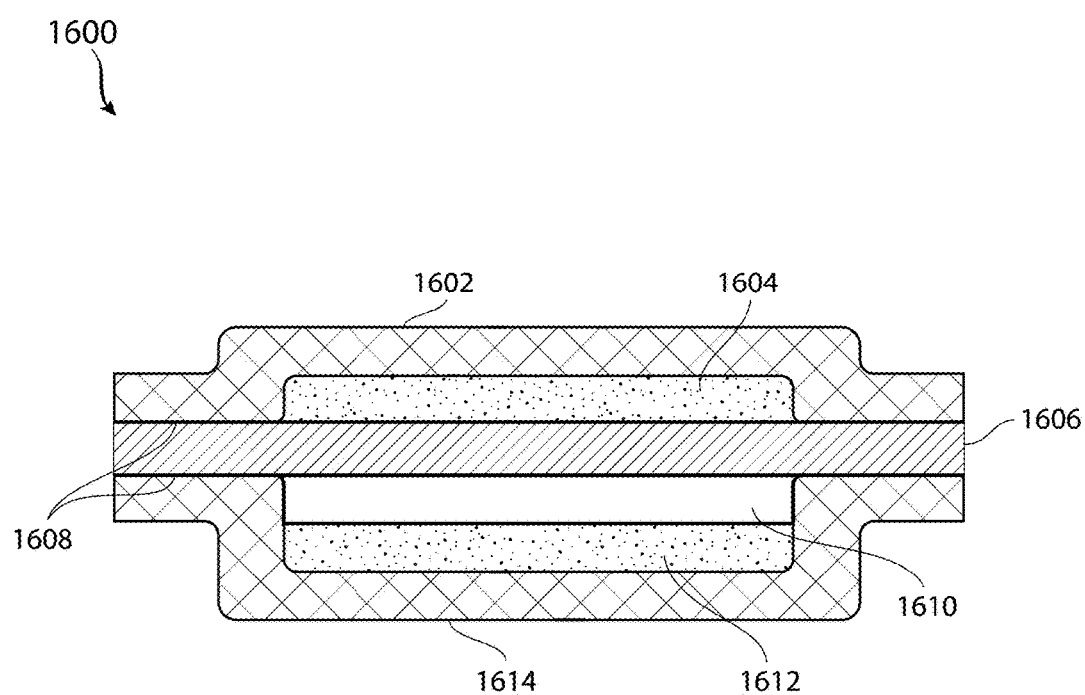
FIG. 16 illustrates an exemplary sensor embodiment.

Referring to FIG. 7, of the exposed view of an alternative design for the Sensor Unit 102 with a pressure sensing band (FIG. 16 will describe pressure sensors in greater detail). FIGS. 7A and 7B depict different views of the same design. The depicted view is for the example implementation in a ski boot, but a similar design could be used for a variety of physical activities. The Sensor Unit 102 includes a force sensing band 706 and a main housing 710. The force sensing band 706 consists of the force sensors 216. The housing 710 consists of the various other components of the Sensor Unit 102

Referring to FIG. 7A, an isometric exposed view of the sensor unit placed on the user's ski boot in accordance with an exemplary embodiment. A housing 710 can be attached to the back of the boot. A force sensing band 702 can be placed between the user's leg and the boot.

Referring to FIG. 7B, a top down exposed view of the sensor unit placed on the user's ski boot in accordance with an exemplary embodiment. A housing 710 can be placed on the back of the boot. A force sensing band 702 can be placed on the inside of the boot between the user's foot and the boot.

Referring to FIG. 7C, an exposed view of the pressure sensing band in accordance with an exemplary embodiment. The force sensing band 702 can be coupled with the housing 710 through the connection 708 which consists of wires encased in a housing material. The pressure sensors 704 can monitor the pressure applied in a given direction. Data from the pressure sensors is gathered by the sensor unit 102. The pressure sensing band is closed by the connector 706 which is used to surround the users leg or attach to the inside of the ski boot. The connector 706 may be made of but not limited to an adhesive, hook and loop fastener or magnets.

Figure 8A:
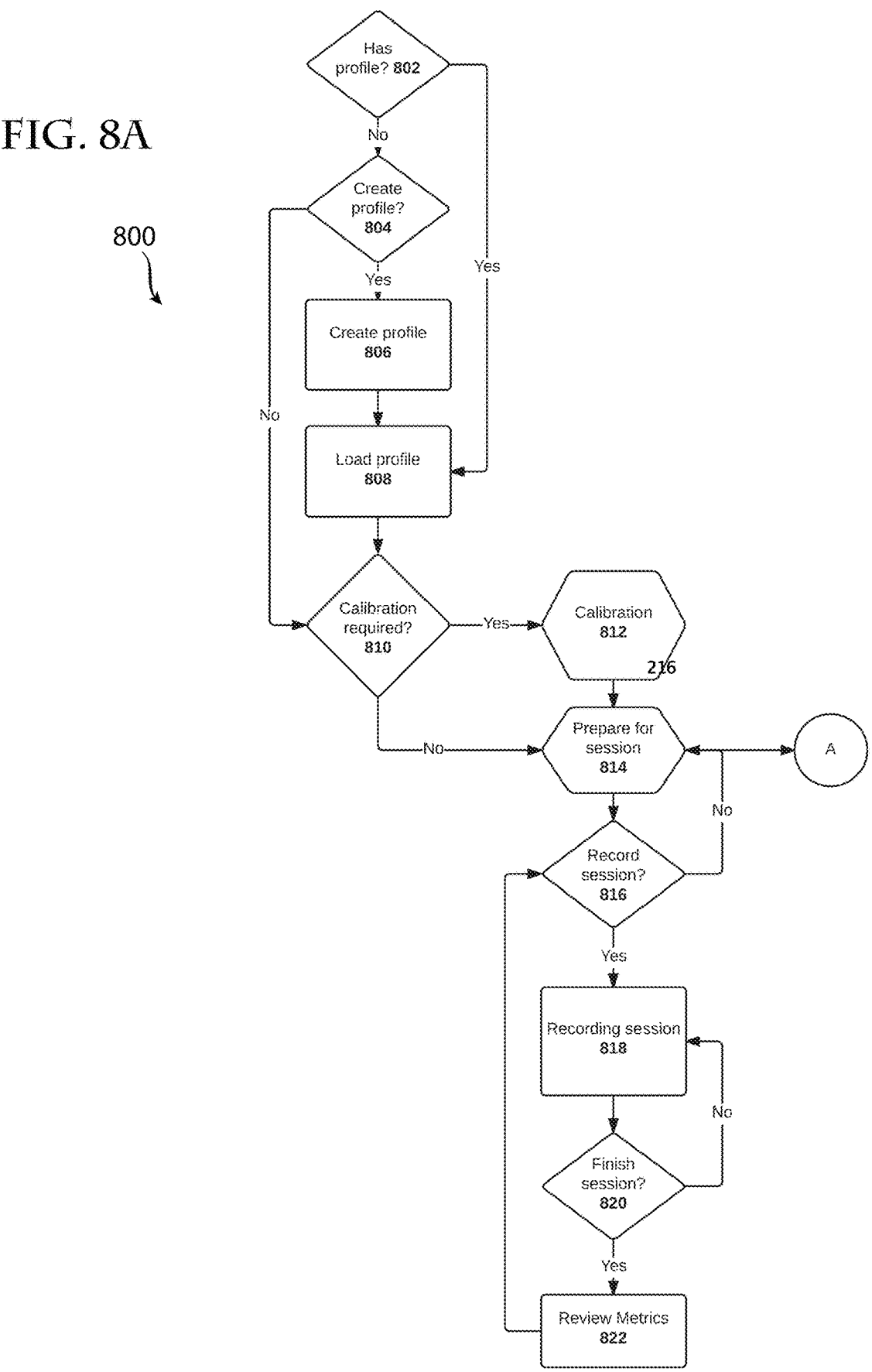
FIGS. 8A and 8B is a flow chart of the user experience in accordance with an exemplary embodiment.
Figure 8B:
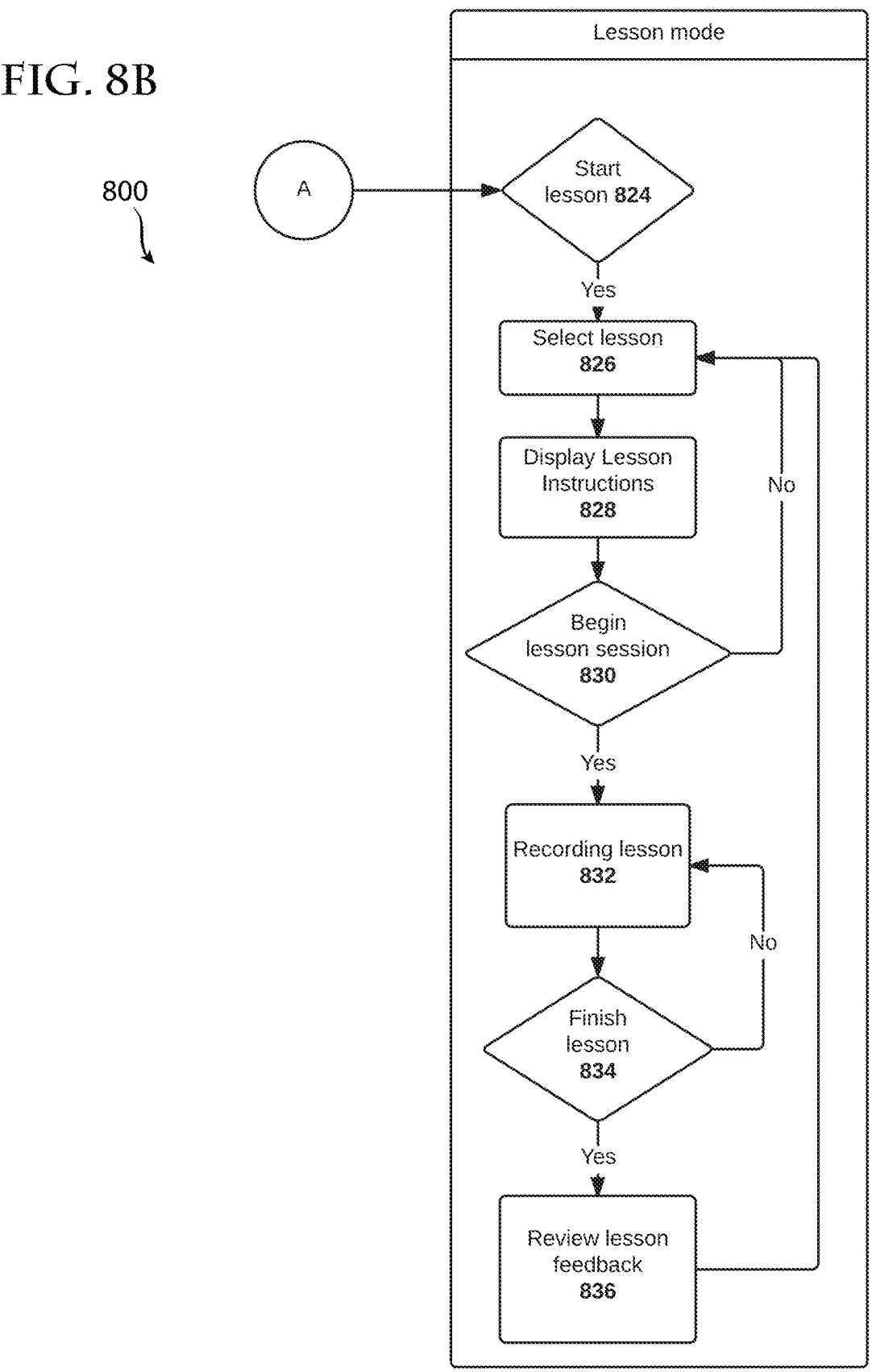

Referring to FIGS. 8A and 8B, a flowchart for the User Interface and User experience on the Feedback Delivery Unit, in accordance with an exemplary embodiment is illustrated. The exemplary method 800 is provided by way of example, as there are a variety of ways to carry out the method. The method 800 described below can be carried out using the configurations illustrated in FIGS. 1-7 and 8-12 by way of example, and various elements of this figure are referenced in explaining exemplary method 800. Each block shown in FIG. 8 represents one or more processes, methods or subroutines, carried out in the exemplary method 800. The exemplary method 800 can begin at block 802. The method 800 also depicts the interaction of the user with the lessons offered by the system. A lesson is defined as the training of the user to achieve a target value for a single performance metric or for several performance metrics.

For example, in skiing, the user may choose to have a lesson to improve their performance metric related to skiing with skis in parallel. Such a lesson will monitor the performance of the user, using Sensor Units 102, in relation to the performance metric and provide them with corrective feedback through the Feedback Delivery Unit 108 in Real-Time. A further example could include a lesson to train the user to have the weighting on the outside ski for each turn, such a lesson would target the left/right bias metric. In boxing, the user may choose lessons to work on footwork, with performance measured based on how the user uses foot pressure and how fast/accurately the user moves their feet.

In this case real-time feedback through headphones could be delivered through the Feedback Delivery Unit 108 whenever the user completes a turn with a large left or right pressure bias. Another example lesson could be based around the forward/backward lean metric. When the user is leaning too far backward for a given threshold of turns the Feedback Delivery Unit 108 reminds the user through the headphones to keep their weight forward in their boots. Another example could include the lead/lag relationship between the skis (where a sensor unit is placed on and/or in each ski and/or boot) and a second sensor associated with the user (either on a ski pole, in a glove, on a watch, in a phone, etc.). In the case where the second sensor is on the upper body, the user would receive positive feedback that the upper body is not leading the turns of the skier. For the case of the physical activity of dancing a lesson could focus on a particular pattern of steps. Each time the user takes the lesson the users path is compared to a known path using the Of Least Squares method, then the user receives feedback from the Feedback Delivery Unit 108 about the parts of their dance step significantly different to the known path.

At block 802, the existence of a user profile is determined. For example, the system determines if the user has a profile or needs to create a user profile. If a user profile exists, the system 800 proceeds to block 808. Otherwise the system proceeds to block 804.

At block 804, the system allows for the creation of a user profile. The profile consists of the username, first and last name, and email address of the user. For example, if the user decides to create a profile, the system proceeds to block 806, otherwise the system proceeds to block 810.

At block 806 the user creates a profile (if necessary). For example, the user enters the details to be associated with their profile and this is stored. This can include data such as height, weight, age, foot/shoe size, boot and/or ski model and manufacturer, and/or even more precise data points such as tibia length, femur length, torso length, chest size, waist size, etc. The method 800 then proceeds to block 808.

At block 808 the users profile is loaded. For example, the performance metrics associated with the user are loaded. After this, the method 800 then proceeds to block 810.

At block 810 the calibration state of the Sensor Unit(s) 102 is checked. The system requests the user to position the sensors in a predetermined orientation, position or location and checks to see if the data correlates with these predetermined configurations. For example, in skiing, the system may ask the user to keep their skis parallel and next to each other and then check if the orientation data from the sensors shows that the skis are parallel. If not, the method 800 initiates a recalibration of the sensors. If calibration is required the method proceeds to block 812. Otherwise the method proceeds to block 814.

At block 814 the system prepares for the recording of a session. For example, the sensor units 102 are switched on and the data begins to be gathered by the Data Collection Unit 104. At this point the user can see the sensor data in real-time. After block 814, the method 800 proceeds to block 816.

At block 816 the user is presented with the option of recording the session when ready. The Feedback Delivery Unit 108 presents the option of recording the session to the user. If the user selects yes then the method proceeds to block 818. Otherwise the method 800 proceeds to block 814.

At block 818 the system records the data. Sensor data from the sensors in the Sensor Unit(s) is saved to storage on the Sensor Unit 102 or the Data Collection Unit 104. At block 818, data is gathered until the system receives a stop command. When the stop command is received, the method 800 proceeds to block 820.

At block 822 the system renders performance metrics calculated from the previous session. For example, the system renders the metrics such as the left/right weight bias of the user or the average and maximum roll of the skis. After block 822 the method 800 then proceeds to block 816.

At block 824 the user is given the option to start a lesson. The lesson mode can give the user real-time feedback on an aspect of performance. If the user selects "start lesson" then the method 800 proceeds to block 826.

At block 826 the user is presented with a number of lessons to aid in the improvement of technique associated with a performance metric. Upon selecting a given lesson the instructions are displayed to the user. The method then proceeds to block 828.

At block 828 the user is presented with instructions on how to improve the selected performance metric. For example, in skiing, the user may have chosen to improve their parallel skiing technique in which case the user is given advice to improve their parallel skiing technique. In snowboarding, the user may have selected to improve turning with their left foot trailing. After this, the method 800 proceeds to block 830.

In block 830 the user is given the option to initiate the lesson. If the user selects "Yes" then the method proceeds to 832. Otherwise the system returns to the select lesson block 826.

In block 832 the method can record the lesson and can provide real-time feedback through the Feedback delivery unit. To use an example for a skiing lesson, the skier could be having a lesson where they are focusing on leaning forward in the boots. During the lesson the force sensors 216 would collect data relating to the position of the skier. This data would then be processed in the Sensor Unit 100, Data Collection Unit 102, or Feedback Delivery Unit 108. When the skier has the correct lean (defined as a threshold front of foot pressure measurement less the back of foot pressure sensor measurement) the feedback can be delivered by 108 this can be done in real-time through the use of headphones, haptic feedback (for embodiments where haptic units are included in the Feedback Delivery Unit(s) 108 and there is the appropriate mechanical contact with the user. The Haptic feedback can be located on the upper body, the insoles, residing in the footwear and/or in the Sensor Unit(s) 102) and/or near eye displays.

As another example, if the user were running, the pressure sensors could detect that the user is performing a heel strike, with an excessive amount of pressure landing on the heel and light pressure on the mid-foot or ball of the foot, and provide real-time feedback to either take shorter strides or land on the ball of the foot. Likewise for runners, if the runner is placing insufficient pressure on the heel, the feedback can provide instructions or otherwise indicate that the user should let the heel slightly touch the ground.

At block 834 the user is given the option to finish the session, if the user selects yes the recording of data and real-time feedback is stopped, then the method proceeds to block 834. Otherwise, the system continues to record data and deliver real-time feedback At block 836 the user is presented with feedback on the lesson. Here the user can understand whether they made progress on the aspect of technique they were trying to focus on. The user can choose to view their progress over different timescales such as the last run, the last day, last week, last ski season or over the lifetime of the product. The value of the performance metric of the user before the lesson is compared with the value of the performance metric after. For example, the left\right bias of the skier is compared before and after the lesson. If the bias has decreased, the technique of the skier has been shown to have improved after the lesson.

Figure 9:
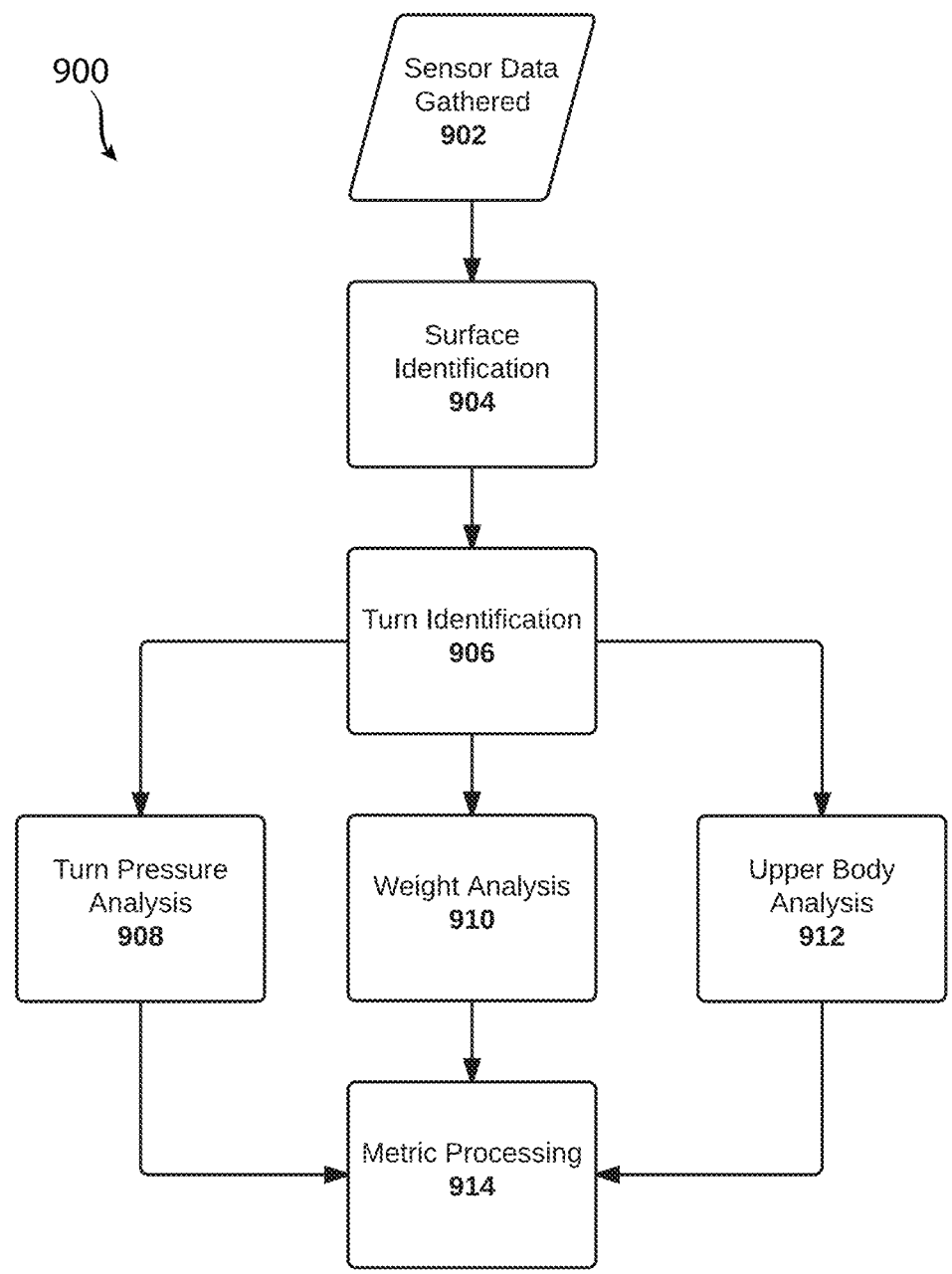
FIG. 9 is a flowchart of a method for processing data in accordance with an exemplary embodiment.

Referring to FIG. 9, a flowchart for the processing of sensor data to generate performance metrics, in accordance with an exemplary embodiment is illustrated. The exemplary method 900 is provided by way of example, as there are a variety of ways to carry out the method. The method 900 described below can be carried out using the configurations illustrated in FIGS. 1-8 and 10-13 by way of example, and various elements of this figure are referenced in explaining exemplary method 900. Each block shown in FIG. 9 represents one or more processes, methods or subroutines, carried out in the exemplary method 900. The exemplary method 900 can begin block 902.

At block 902 the system gathers data. For example, data from multiple sensors including 204, 206, 208, 216, 218, 220 and 222 across a plurality of sensor units 102 are gathered by the Data Collection Unit 104. After Block 902, the method 900 proceeds to block 904.

At block 904 the surface is identified. For example, the system uses the data from the sensors 220 and 204 to identify the surface using method 1000. The calculation to identify the surface can be done by the processor 210 of the data collection unit 104 and/or by the server 106. After identifying the surface, the method 900 proceeds to block 906.

At block 906 the turns of the user are identified to give context to performance metrics. The turns are identified using sensor data from sensors including 204, 206, 208, and 222 using the process described in FIG. 12. Block 904 proceeds to block 908, block 910 and block 912.

At block 908 turn pressure is analyzed. The analysis of the pressure along the turn is done using the methods in block 410. After block 908, the method 900 proceeds to block 914.

At block 910 the system analyses the data gathered related to the weight. Methods stated in block 410 are used. After block 908, the method 900 proceeds to block 914. At block 912 the gathered data is used to model the upper body. An example embodiment for a skier could be to compare the yaw of the skis to that of the upper body. This embodiment would allow the calculation of the magnitude of covariance of upper body yaw compared to ski yaw as well as the measurement of lead/lag relationship listed in examples of possible performance metrics. After block 912, the method 900 proceeds to block 914. At block 914 the metrics are stored. For example, the metrics calculated from the previous steps are stored in the storage unit 300.

Figure 10A:
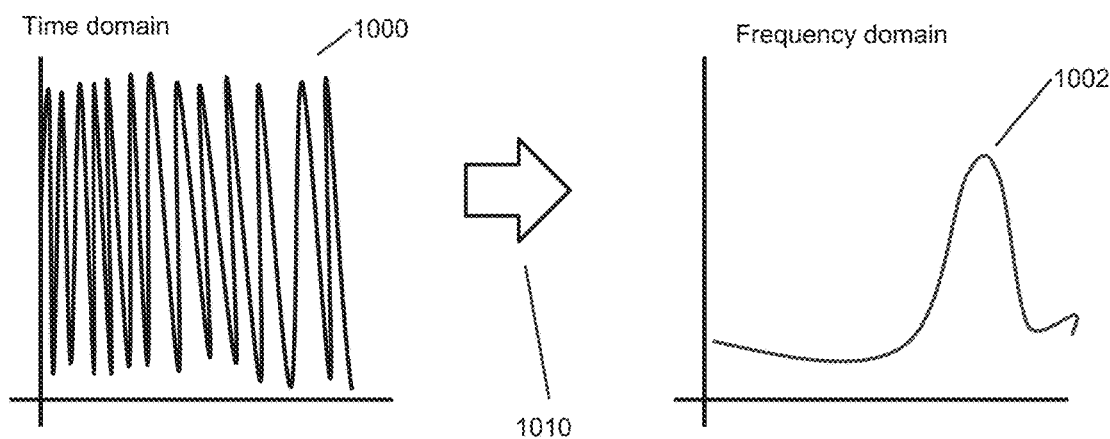
FIGS. 10A and 10B illustrate an overview of a method to identify a type of surface a user is in contact with in accordance with an exemplary embodiment.
Figure 10B:
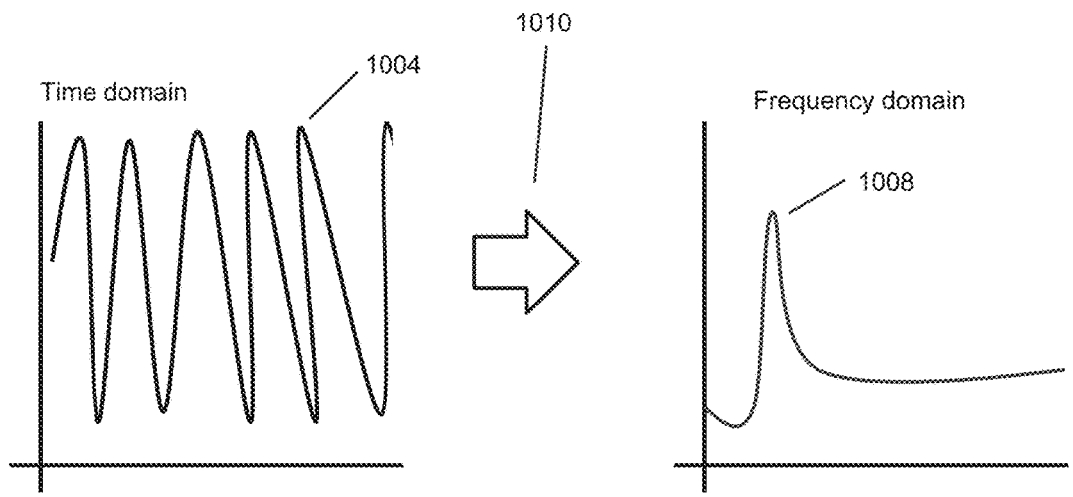

Referring to FIG. 10, a graph of the motion or audio data in the time and frequency domain in accordance with an exemplary embodiment is illustrated. Using the Fourier Transform, or any such similar transform, the user performance metrics can be classified by the surface. For example, in the case of cycling, the method can be used to differentiate between when the cyclist is on a rough or smooth road. Calculating performance metrics for both these two contexts allows the cyclist to understand the effect of road surface on performance. To give another example, in the case of skiing, contextual information is important to differentiate performance between skiing on powder, ice, packed snow and granular ice. The method can take place in the processing components of the Sensor Unit 102, the Data Collection Unit 104 or Server 106. The method can be based on data from the Accelerometer 204, Magnetometer 206, Gyroscope 208, and Barometer 218, High Frequency Microphone 220 or Force Sensors 216 or any combination thereof. For the example case given in FIG. 10 of an accelerometer, the data for a rough and smooth surface is denoted by 1000 and 1004, respectively. Once the Fourier transform is taken the peak can be found by finding the maximum in the frequency domain. To classify the surface the peak can be compared to frequency domain peaks for known surfaces. The peak is classified by calculating the squared difference between peaks of known surfaces. The classified surface will be that with the lowest squared difference in peak frequency. Although FIG. 10 provides a specific example of a Fourier transform combined with an Of Least Squares classifier other combinations could equally be applied such as Fourier or other time-series features with supervised (For instance artificial neural network, Bayesian statistics or support vector machines) or unsupervised learning (Such as expectation-maximization algorithm, vector quantization, generative topographic map, or the information bottleneck method).

Figure 11:
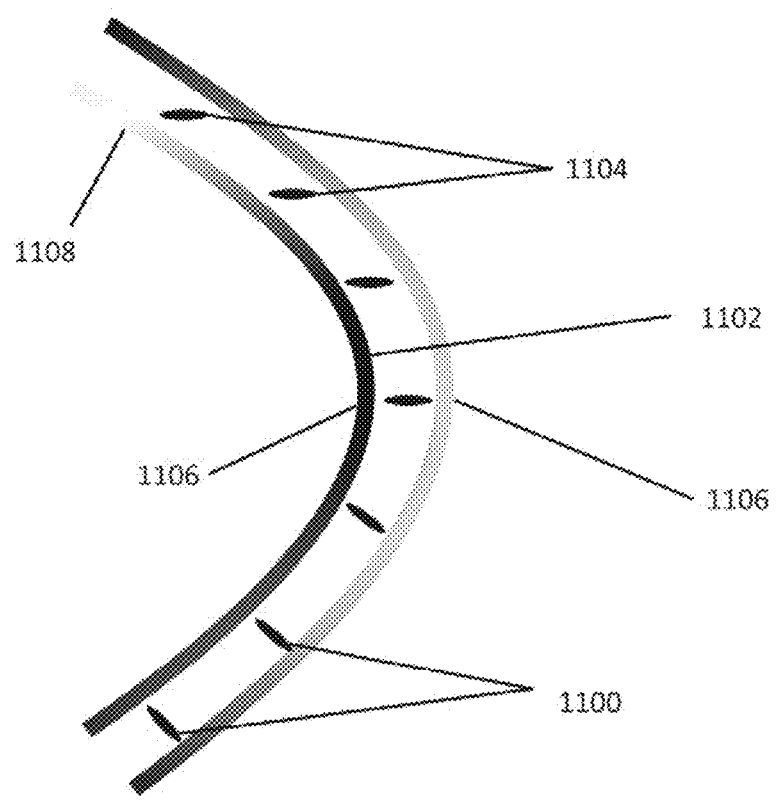
FIG. 11 is a block diagram of a user interface in accordance with an exemplary embodiment.

Referring to FIG. 11, a screenshot showing foot pressure and upper body orientation at different points during a path of a user, in accordance with an exemplary embodiment. As shown, the path is for a skier making a turn. One of ordinary skill in the art would understand that other user activities can be displayed, such as, but not limited to, climbing a hill on a bicycle, a jump in ballet or the foot pressure at different points in the steps of a dance. The illustration depicted in FIG. 11 is suitable for many activities where the foot pressure varies at different points of the path of the user. FIG. 11 depicts the pressure of different points in the turn of a skier, but the same technique could also be for other activities. To generate the image, data from the Accelerometer 204, Magnetometer 206, Gyroscope 208 and process orientation calculation as well as Global Positioning System (GPS) 222 or 308 to give a representation of the path of the user can be combined. Overlaid on the path of the user is the foot pressure recorded from the Force Sensors 216. The components of the turn where the user is placing greater pressure have a darker color. For the path depicted in FIG. 11 the user places a stronger pressure at the center of the turn for the inside foot 1108, denoted by the darker shading. For the outside foot 1106 the pressure is slighter with lighter shading.

FIG. 11 also contains representations of the user's upper body labelled 1100 and 1104. The data for the representation is done by comparing processed data gathered by the Data Collection Unit 104 from the Sensor Units 102 placed on the Upper Body and the Insoles of the user. The data from the motion sensors 310 and 204/206/208 are processed to give the orientation of the users body using a Sensor Fusion algorithm. The yaw of the skiers body can be taken from the output of the Sensor Fusion and is used to display the representations of the upper body shown in 1100 and 1104. In 1100 the user's body is facing the direction of the lower body, in 1104 the user is keeping their body facing directly forward.

Figure 12A:
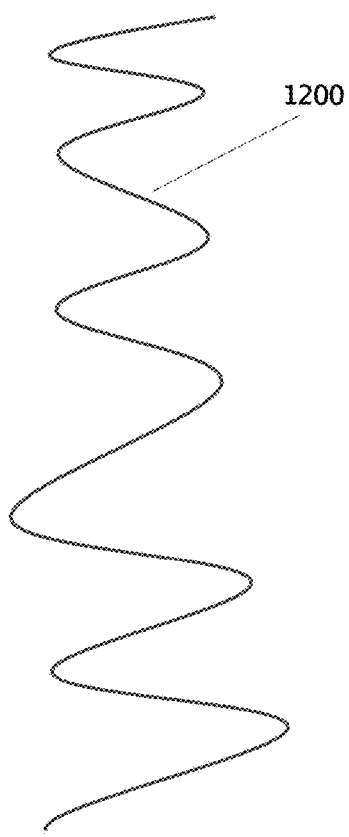
FIGS. 12A and 12B illustrate an overview of a method to identify turns in the motion of a user in accordance with the exemplary embodiment.
Figure 12B:
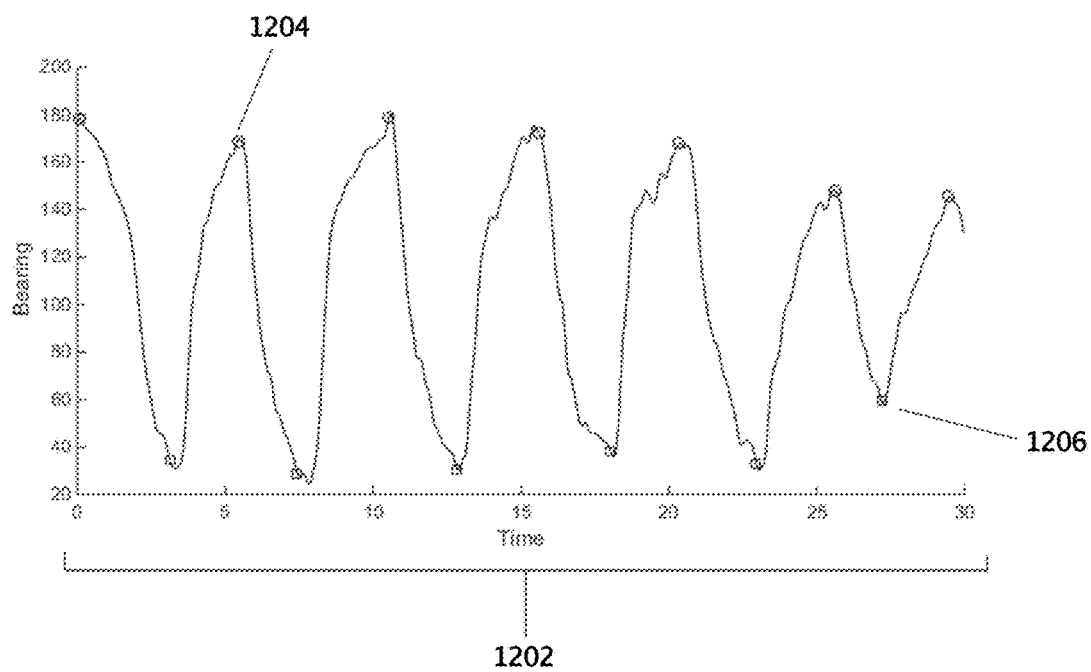

Referring to FIGS. 12A and 12B, a skier's path is shown in accordance with an exemplary embodiment and a screenshot showing the pressure and motion data in accordance with an exemplary embodiment is illustrated. The feature to identify turns is important to give the context to the pressure and motion data. The average yaw of the user's feet is calculated using a motion fusion algorithm using the motion data gathered by the Data Collection Unit 104 from the Sensor Units 102 containing the sensors 204, 206, 208, 218, and 222. FIG. 12a shows the path of a user 1200 and a corresponding graph 1202 of the average yaw of the user's feet is shown in FIG. 12b. The portrayed embodiment measures the peaks 1204 and troughs 1206 of the yaw as the beginning and end of the turn. An equivalent technique could be applied for the roll and/or pitch of the user's feet with the identification of the same or different data features. The method can be conducted in the processing components of the Sensor Unit 100, Data Collection Unit 102, Server 104 or Feedback Delivery Unit 110.

Figure 13:
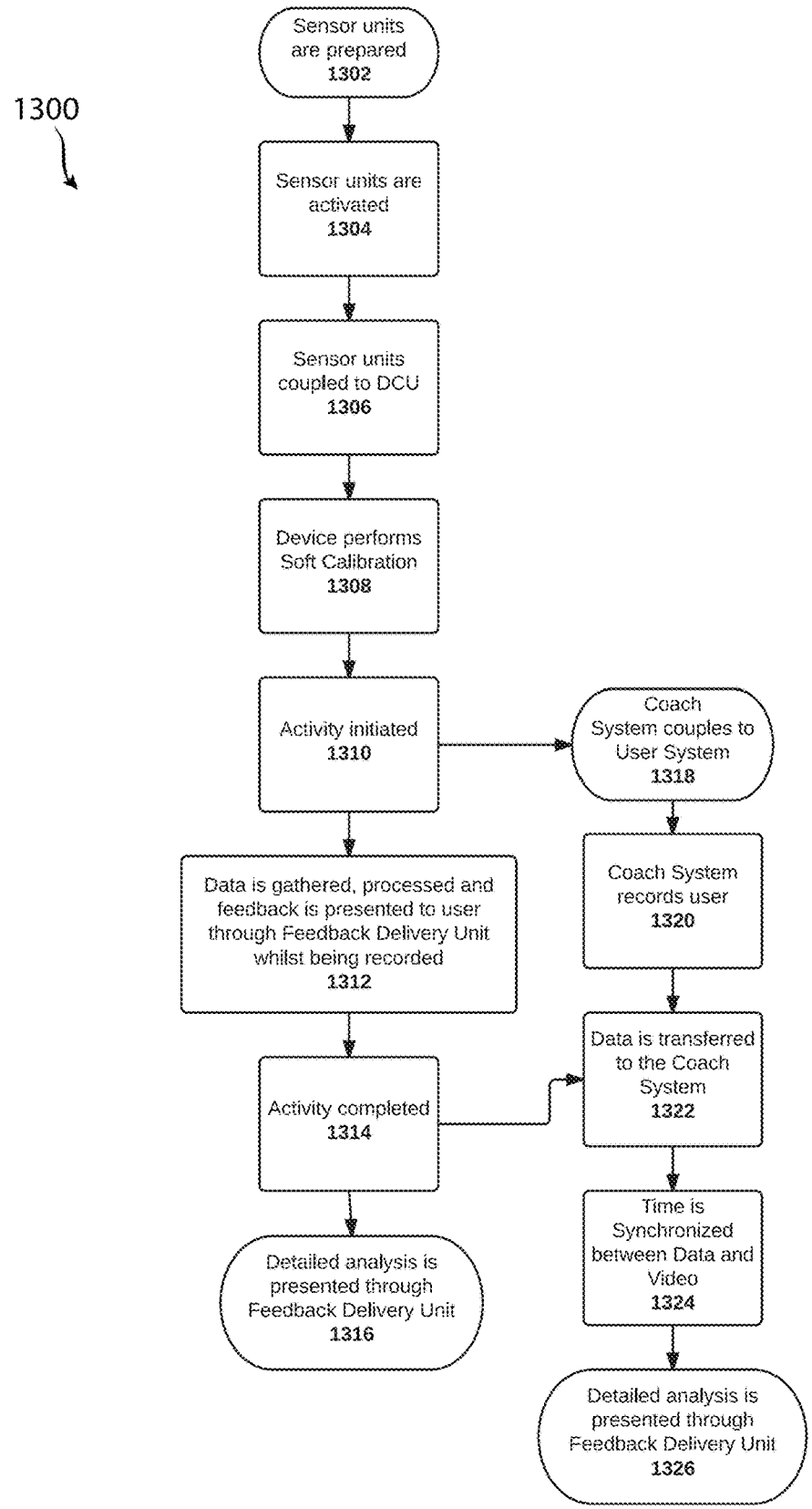
FIG. 13 is a flowchart of a method for the user experience and interaction between a user and their coach or trainer.

Referring to FIG. 13, a flowchart for suggested interactions when using the system with a human coach, in accordance with an exemplary embodiment is illustrated. The coach system consists of an application running on a mobile phone or tablet PC. The coach system allows the coach to track a user's performance by viewing their performance metrics over time. The coach system also allows the coach to record a video of the user and synchronize the video with the data from the user. The exemplary method 1300 is provided by way of example, as there are a variety of ways to carry out the method. The method 1300 described below can be carried out using the configurations illustrated in FIGS. 1-12 by way of example, and various elements of this figure are referenced in explaining exemplary method 1300. Each block shown in FIG. 13 represents one or more processes, methods or subroutines, carried out in the exemplary method 1300. The exemplary method 1300 can begin block 1302.

At block 1302, the system is prepared. For example, the user attaches the Sensor Units 102 to various points on the body and equipment. For example, for a skier, Sensor Units 102 could be placed on the each of the boots and the upper body of the user. In other embodiments, a Sensor Unit 102 could be included in the skier's ski poles. If the user were a boxer, a Sensor Unit 102 could be placed in the boxing gloves. As the user hits, data can be collected regarding (1) how hard the user has hit and (2) where on the user's hand the contact was initiated. After being prepared, the system 1300 proceeds to block 1304

At block 1304, the system is activated. For example, the user switches on the Sensor Units 102. Block 1304 proceeds to block 1306.

At block 1306, the system is internally coupled, meaning the Sensor Units 102 are coupled with the Data Collection Unit 104, such that the Data Collection Unit records the data being collected at the sensor. Such coupling can occur automatically, or can be user initiated. For example, a user can select to couple the Sensor Units 102 with the Data Collection Unit 104 via Bluetooth or other mechanisms. In other configurations, the sensor can automatically couple to a nearby data collection unit. After block 1306, method 1300 proceeds to block 1308.

At block 1308, the system is calibrated. For example, a user engages the Data Collection Unit 104 to calibrate the Sensor Units 102. This could include certain movements or requiring the user to place the sensor units in a certain direction. After block 1308, method 1300 proceeds to block 1310.

At block 1310, the user engages in the physical activity. For example, for skiing, the user would begin to ski. For horse riding, the user could begin to ride. At this time the method proceeds to block 1312 and 1318.

At block 1312, data is gathered, processed and feedback is presented by the system. For example, the Data Collection Unit 104 gathers data from the Sensor Units 102. This is processed by the Data Collection Unit 104 and then presented by the Feedback Delivery Unit 108. After block 1312, the system 1300 proceeds to block 1314.

At block 1314, the activity is completed. For example, the data would stop being gathered. After block 1314, the system 1300 proceeds to block 1316.

At block 1316, detailed analysis is rendered and presented by the system. For example, the Data Collection Unit 104 would process the gathered data and present detailed analysis through the Feedback Delivery Unit.

At block 1318 the Coach System and User system are coupled, such that the activity coach identifies the user and has access to the data of the Data Collection Unit 104. Method 1300 then proceeds to block 1320.

At block 1320 the coach system records the user. For example, the coach records the user with a video camera. This could be a traditional camera, or a smartphone or tablet PC camera. When the user finishes the activity method 1300 proceeds from 1320 to 1322.

At block 1322, the data from the system is transferred to the Coach System. For example, the gathered and processed data from the Data Collection Unit 104, is transmitted to the Coach System through a wired connection or wireless connection via Wi-Fi, Bluetooth or any other Radio frequency. After block 1322, the system 1300 proceeds to 1324.

At block 1324 the filmed data from the instructor is synchronized with the data of the user. The data can be synchronized by displaying a timestamp from the Data Collection Unit 104 to the video camera, using an audio signal or using a wireless signal such as Bluetooth, Wi-Fi between the coach's smartphone or tablet PC. Alternatively, the synchronization can be conducted using an internet clock or a global positioning system. Once synchronization is completed the method 1300 can continue to block 1326.

At block 1326 the feedback delivery unit 108 renders a detailed level of analysis with the recorded video footage of the user performing the activity. The recorded footage of the user can be augmented with, or alongside, sensor and processed sensor data.

Figure 14:
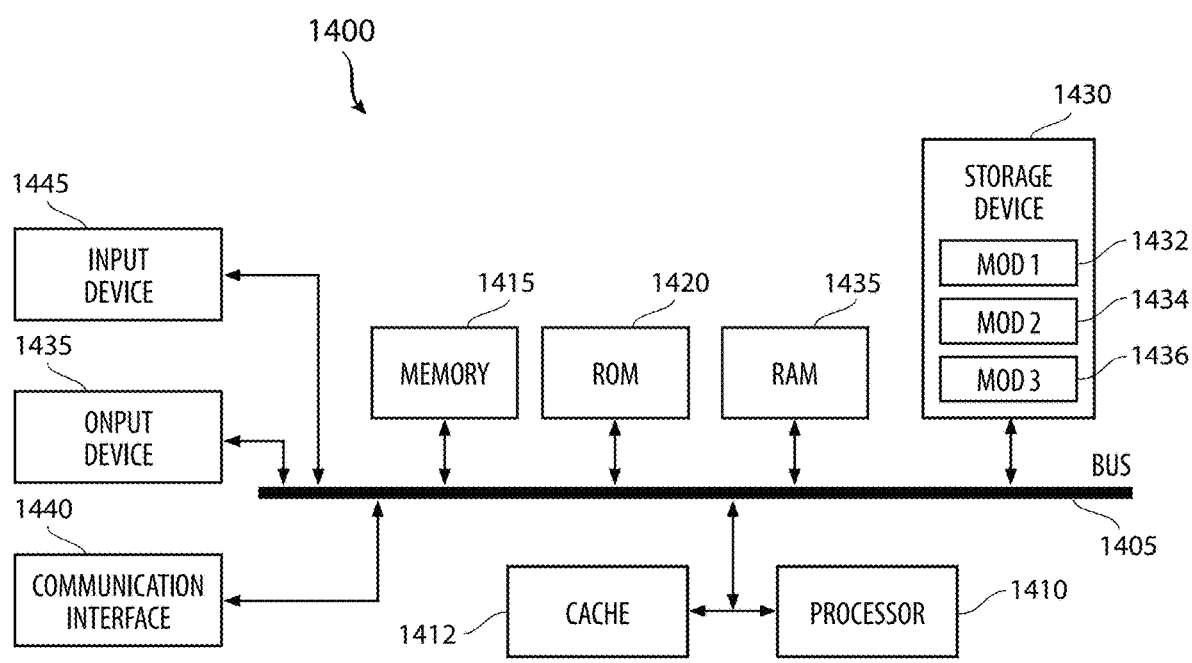
FIG. 14 illustrates an exemplary computer system.

FIG. 14 provides a brief introductory description of a basic general purpose system or computing device which can be employed to practice the concepts is disclosed herein. The exemplary system 1400 includes a general-purpose computing device, including a processing unit (CPU or processor) 1410 and a system bus 1405 that couples various system components including the system memory 1415 such as read only memory (ROM) 1420 and random access memory (RAM) 1435 to the processor 1410. The system 1400 can include a cache 1412 of high speed memory connected directly with, in close proximity to, or integrated as part of the processor 1410. The system 1400 copies data from the memory 1415 and/or the storage device 1430 to the cache 1412 for quick access by the processor 1410. In this way, the cache provides a performance boost that avoids processor 1410 delays while waiting for data. These and other modules can control or be configured to control the processor 1410 to perform various actions. Other system memory 1415 may be available for use as well. The memory 1415 can include multiple different types of memory with different performance characteristics. It can be appreciated that the disclosure may operate on a computing device 1400 with more than one processor 1410 or on a group or cluster of computing devices networked together to provide greater processing capability. The processor 1410 can include any general purpose processor and a hardware module or software module, such as module 1 1432, module 2 1434, and module 3 1436 stored in storage device 1430, configured to control the processor 1410 as well as a special-purpose processor where software instructions are incorporated into the actual processor design. The processor 1410 may essentially be a completely self-contained computing system, containing multiple cores or processors, a bus, memory controller, cache, etc. A multi-core processor may be symmetric or asymmetric.

The system bus 1405 may be any of several types of bus structures including a memory bus or memory controller, a peripheral bus, and a local bus using any of a variety of bus architectures. A basic input/output (BIOS) stored in ROM 1420 or the like, may provide the basic routine that helps to transfer information between elements within the computing device 1400, such as during start-up. The computing device 1400 further includes storage devices 1430 such as a hard disk drive, a magnetic disk drive, an optical disk drive, or tape drive. The storage device 1430 can include software modules 1432, 1434, 1436 for controlling the processor 1410. Other hardware or software modules are contemplated. The storage device 1430 is connected to the system bus 1405 by a drive interface. The drives and the associated computer-readable storage media provide nonvolatile storage of computer-readable instructions, data structures, program modules and other data for the computing device 1400. In one aspect, a hardware module that performs a particular function includes the software component stored in a tangible computer-readable storage medium in connection with the necessary hardware components, such as the processor 1410, bus 1405, display 1435, and so forth, to carry out the function. In another aspect, the system can use a processor and computer-readable storage medium to store instructions which, when executed by the processor, cause the processor to perform a method or other specific actions. The basic components and appropriate variations are contemplated depending on the type of device, such as whether the device 1400 is a small, handheld computing device, a desktop computer, or a computer server.

Although the exemplary embodiment described herein employs the hard disk 1430, other types of computer-readable media which can store data that are accessible by a computer, such as magnetic cassettes, flash memory cards, digital versatile disks, cartridges, random access memories (RAMs) 1435, and read only memory (ROM) 1420, may also be used in the exemplary operating environment. Tangible computer-readable storage media, computer-readable storage devices, or computer-readable memory devices, expressly exclude media such as transitory waves, energy, carrier signals, electromagnetic waves, and signals per se.

To enable user interaction with the computing device 1400, an input device 1445 represents any number of input mechanisms, such as a microphone for speech, a touch-sensitive screen for gesture or graphical input, keyboard, mouse, motion input, speech and so forth. An output device 1435 can also be one or more of a number of output mechanisms known to those of skill in the art. In some instances, multimodal systems enable a user to provide multiple types of input to communicate with the computing device 1400. The communications interface 1440 generally governs and manages the user input and system output. There is no restriction on operating on any particular hardware arrangement and therefore the basic features here may easily be substituted for improved hardware or firmware arrangements as they are developed.

For clarity of explanation, the illustrative system embodiment is presented as including individual functional blocks including functional blocks labeled as a "processor" or processor 1410. The functions these blocks represent may be provided through the use of either shared or dedicated hardware, including, but not limited to, hardware capable of executing software and hardware, such as a processor 1410, that is purpose-built to operate as an equivalent to software executing on a general purpose processor. For example the functions of one or more processors presented in FIG. 14 may be provided by a single shared processor or multiple processors. Illustrative embodiments may include microprocessor and/or digital signal processor (DSP) hardware, read-only memory (ROM) 1420 for storing software performing the operations described below, and random access memory (RAM) 1435 for storing results. Very large scale integration (VLSI) hardware embodiments, as well as custom VLSI circuitry in combination with a general purpose DSP circuit, may also be provided.

The logical operations of the various embodiments are implemented as: (1) a sequence of computer implemented steps, operations, or procedures running on a programmable circuit within a general use computer, (2) a sequence of computer implemented steps, operations, or procedures running on a specific-use programmable circuit; and/or (3) interconnected machine modules or program engines within the programmable circuits. The system 1400 shown in FIG. 14 can practice all or part of the recited methods, can be a part of the recited systems, and/or can operate according to instructions in the recited tangible computer-readable storage media. Such logical operations can be implemented as modules configured to control the processor 1410 to perform particular functions according to the programming of the module. For example, FIG. 14 illustrates three modules Mod1 1432, Mod2 1434 and Mod3 1436 which are modules configured to control the processor 1410. These modules may be stored on the storage device 1430 and loaded into RAM 1435 or memory 1415 at runtime or may be stored in other computer-readable memory locations.

Figure 15:
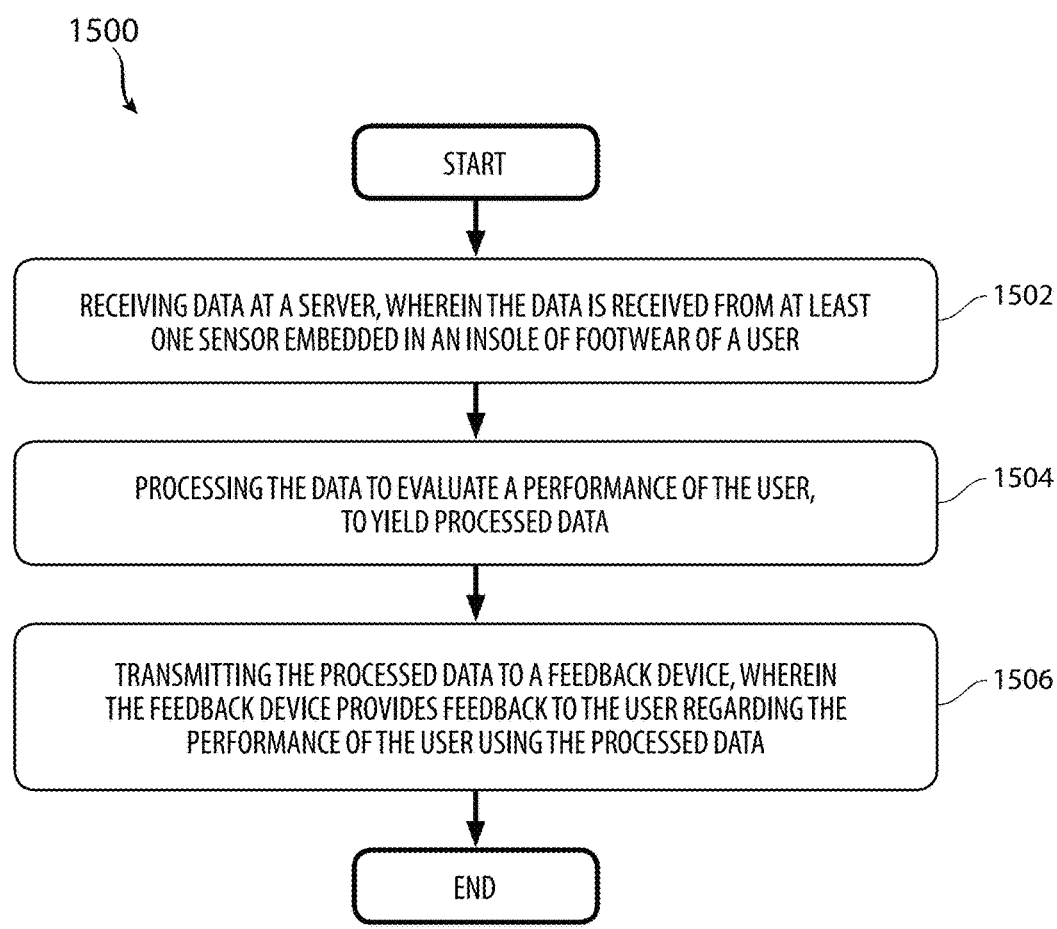
FIG. 15 illustrates an example method embodiment.

Having disclosed some components of a computing system, the disclosure now turns to FIG. 15, which illustrates an exemplary method embodiment. For the sake of clarity, the method is described in terms of an exemplary system 1400 as shown in FIG. 14 configured to practice the method. The steps outlined herein are exemplary and can be implemented in any combination thereof, including combinations that exclude, add, or modify certain steps.

The system 1400 receives data at a sever, wherein the data is received from at least one sensor embedded in an insole of footwear of a user (1502). In other embodiments, the data can be received from at least one sensor in footwear of a user, where the at least one sensor is located between a foot of the user and a sole of the footwear. Exemplary footwear of the user can include a ski boot, a snowboarding boot, a water skiing boot, a wakeboarding boot, a tennis shoe, an ice skate, a golf shoe, a rowing shoe, and a horse riding boot. The system 1400 processes the data to evaluate a performance of the user, to yield processed data (1504), and transmits the processed data to a feedback device, wherein the feedback device provides feedback to the user regarding the performance of the user using the processed data (1506).

In certain configurations, processing the data to evaluate the performance of the user can further include: identifying a pressure applied to the at least one sensor by a foot of the user; identifying a position and an orientation of the user; and comparing the pressure, the position, and the orientation to a best practice threshold. In other configurations, processing the data to evaluate the performance of the user can also include: combining the processed data with a video analysis of a recording of the performance of the user.

While the system 1400 can operate entirely using sensors in the user's footwear, the user can have additional sensors on their person, which are not associated with the footwear, and the system 1400 can receive additional data from these additional sensors, then utilize this additional data during the processing of the data/evaluation of the user's performance. For example, an additional sensor can be embedded in a glove, goggles, a ski pole, boxing glove, golf club, rowing oar, etc.

Certain configurations of the system 1400 allow for the user to select lessons to hone specific aspects of performance. In addition, the system 1400 can suggest lessons to the user based on their performance. Such suggestions can be based on previous performances which may or may not be associated with lessons. For example, if the user has taken a lesson and excelled in a subsequent performance, the system 1400 can suggest a higher-level lesson, whereas if the user's subsequent performance is poor then the system 1400 can suggest returning to a lower-level/basic lesson before returning to the current lesson level. The system 1400 can compare performances (and scores/rankings based on performances) after lessons.

The feedback device can provide the feedback while the user continues the performance. Exemplary feedback devices can include an audio feedback device, a haptic feedback device, and near-eye display feedback. One non-limiting example of feedback is a user-interface with an infographic, where the infographic is color coded along a path of the user according to pressure being applied. As a first example, the path could be colored red on those portions of the path where the user is applying/applied incorrect pressure and green on those portions of the path where the user applied correct pressure. As a second example, the path could be colored red where the user applied heavy pressure and green where pressure was lightly applied.

FIG. 16 illustrates an exemplary sensor embodiment 1600. More specifically, FIG. 16 illustrates a cross-sectional view of an insole or insert either wholly or partly embodying the Sensor Unit 102. As shown, the Sensor Unit 102 is in part made up of a composite including a waterproof fabric cover 1602, a conductive layer 1604 that could be embodied by a conductive fabric, a layer of copper, printed conductive ink or deposited conductive material, an elastomer 1606, a Flexible Printed Circuit (FPC) 1610, another conductive layer 1612 and another waterproof fabric cover 1614. In this embodiment 1600, the layers are bonded together with an adhesive 1608. The FPC 1610 can have capacitance sensors soldered, molded, or otherwise built into the FPC 1610. The FPC 1610 can have, for example, local processing chips for processing data collected by the Sensor Unit 102. The cover layers 1602, 1614 and the dielectric 1606 can, in some configurations, be larger than the conductive fabric layers 1604, 1612 and the FPC 1610, allowing for trimming back or forming the sensor 1600 to specific requirements.

The composite forms a pressure sensing device by measuring the capacitance between pads on the FPC 1610 to the grounded conductive fabric 1604, 1612. As orientated in FIG. 16, vertical pressure on the composite causes the elastomer 1606 to compress, increasing the capacitance between the FPC 1610 and the conductive fabric 1612. In one variation of 1600, the adhesive 1608 may be formed by a heated weld which bonds the elastomer 1606 and both waterproof fabric covers 1602, 1614.

Figure 17:
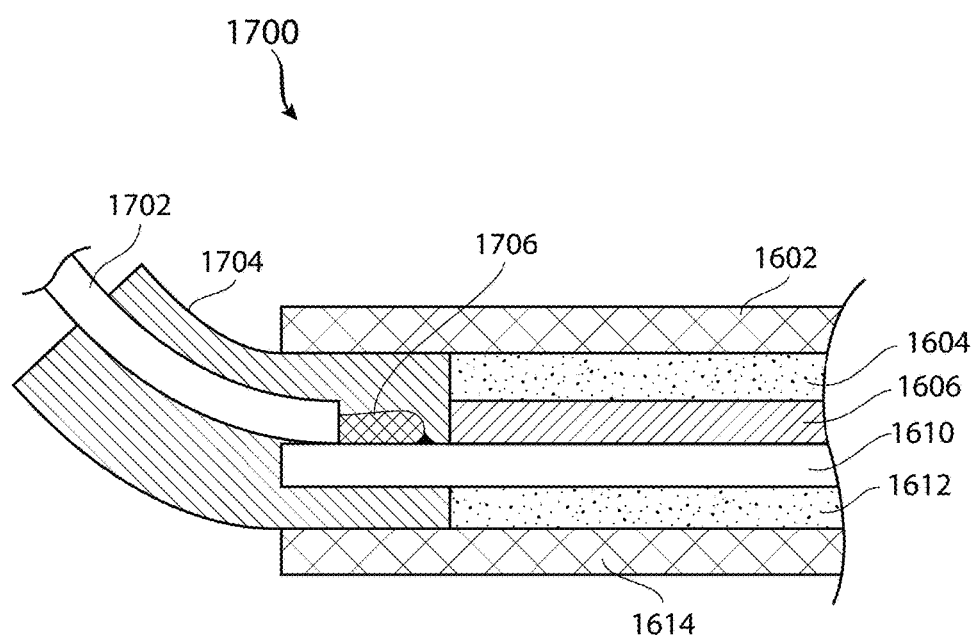
FIG. 17 illustrates an exemplary sensor embodiment connected to a wire.

FIG. 17 illustrates an exemplary sensor embodiment 1700 similar to the sensor illustrated in FIG. 16, but in this instance the illustrated sensor is connected to a wire 1702. Here, the capacitance sensing pads on the FPC 1610 are connected to microchips on the FPC 1610 that measure the capacitance and convert it to a digital signal. These microchips are placed as close as possible to the pads so as to reduce the effect of any stray capacitance on the tracks connecting to the pads. The cable/wire 1702 connecting the sensor 1600 to the microchips can be insulated, having an overmolded cable guide 1704. The conductive center 1706 of the wire 1702 connects with the FPC 1610 (i.e., there is no insulation where the data is communicated with the wire 1702 from the sensor). The cables can be connected to the insole using the overmolded cable guide 1704. An alternative design can use a molded cable guide that is bonded to the FPC 1610 using adhesive and to the fabric cover 1602, 1614 using a heated weld. The two layers of conductive fabric 1604, 1612 can be electrically connected to ground through the FPC 1610 by a conductive adhesive.

Figure 18:
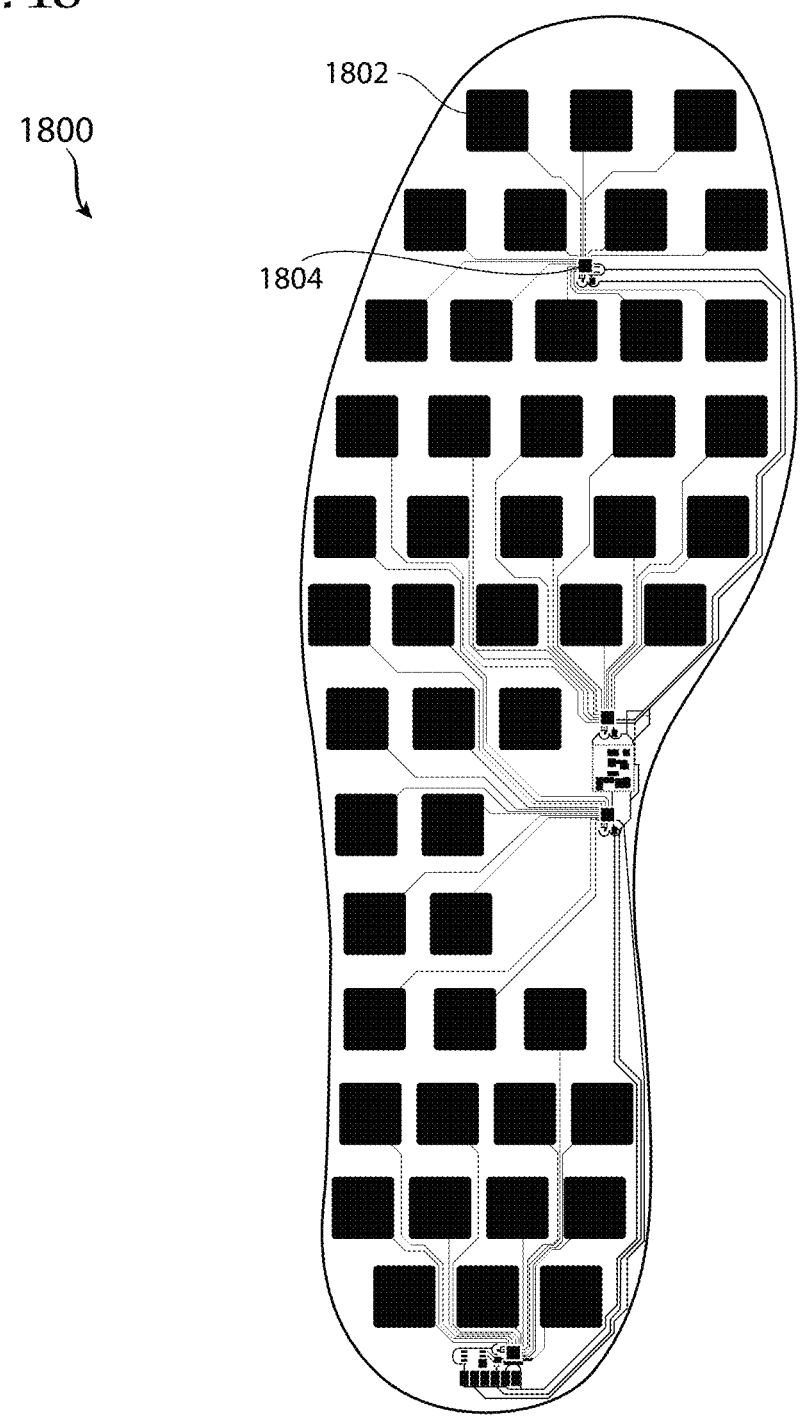
FIG. 18 illustrates an exemplary array of sensors for deployment in footwear.

FIG. 18 illustrates an exemplary array of sensors for deployment in footwear 1800. As illustrated, the array has a plurality of sensors 1802 connected by cables 1804 to microchips. Such an array can, for example, be inserted into a shoe above or below the standard insole of a shoe or boot, and allows collection of pressure related data as discussed above.

Embodiments within the scope of the present disclosure may also include tangible and/or non-transitory computer-readable storage media for carrying or having computer-executable instructions or data structures stored thereon. Such tangible computer-readable storage media can be any available media that can be accessed by a general purpose or special purpose computer, including the functional design of any special purpose processor as described above. By way of example, and not limitation, such tangible computer-readable media can include RAM, ROM, EEPROM, CD-ROM or other optical disk storage, magnetic disk storage or other magnetic storage devices, or any other medium which can be used to carry or store desired program code means in the form of computer-executable instructions, data structures, or processor chip design. When information is transferred or provided over a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable media.

Computer-executable instructions include, for example, instructions and data which cause a general purpose computer, special purpose computer, or special purpose processing device to perform a certain function or group of functions. Computer-executable instructions also include program modules that are executed by computers in stand-alone or network environments. Generally, program modules include routines, programs, components, data structures, objects, and the functions inherent in the design of special-purpose processors, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

Other embodiments of the disclosure may be practiced in network computing environments with many types of computer system configurations, including personal computers, hand-held devices, multi-processor systems, microprocessor-based or programmable consumer electronics, network PCs, minicomputers, mainframe computers, and the like. Embodiments may also be practiced in distributed computing environments where tasks are performed by local and remote processing devices that are linked (either by hardwired links, wireless links, or by a combination thereof) through a communications network. In a distributed computing environment, program modules may be located in both local and remote memory storage devices.

The embodiments shown and described above are only examples. Therefore, many details are neither shown nor described. Even though numerous characteristics and advantages of the present technology have been set forth in the foregoing description, together with details of the structure and function of the present disclosure, the disclosure is illustrative only, and changes may be made in the detail, especially in matters of shape, size and arrangement of the parts within the principles of the present disclosure to the full extent indicated by the broad general meaning of the terms used in the attached claims. It will therefore be appreciated that the embodiments described above may be modified within the scope of the appended claims.

The various embodiments described above are provided by way of illustration only and should not be construed to limit the scope of the disclosure. For example, the principles herein can be applied to pressure measurements in a wide variety of sports, activities, and performances. Various modifications and changes may be made to the principles described herein without following the example embodiments and applications illustrated and described herein, and without departing from the spirit and scope of the disclosure.

Statement Bank

Statement 1: A method comprising: measuring data using at least one sensor, wherein the data is received from the at least one sensor in footwear of a user, the at least one sensor being located between a foot of the user and a sole of the footwear; processing the data to evaluate a performance of the user, to yield processed data; and transmitting the processed data to a feedback device, wherein the feedback device provides feedback to the user regarding the performance of the user using the processed data.

Statement 2: The method of Statement 1, wherein the footwear of the user comprises a snow ski boot.

Statement 3: The method of Statement 1 or 2, wherein the footwear of the user comprises one of a snowboarding boot, a water skiing boot, a wakeboarding boot, an ice skate, a golf shoe, a rowing shoe, a horse riding boot, and a cycling shoe.

Statement 4: The method of any of the above statements, wherein the processing of the data to evaluate the performance of the user further comprises: identifying a pressure applied to the at least one sensor by a foot of the user; identifying a position and an orientation of the user; and comparing the pressure, the position, and the orientation to a best practice threshold.

Statement 5: The method of any of the above statements, wherein the processing of the data to evaluate the performance of the user further comprises: combining the processed data with a video of the performance of the user.

Statement 6: The method of any of the above statements, further comprising receiving second data from a second sensor associated with the user, wherein the second sensor is not associated with the footwear; and utilizing the second data during the processing of the data.

Statement 7: The method of any of the above statements, wherein the second sensor is embedded in one of a ski pole, a helmet, a snow glove, and a goggle.

Statement 8: The method of any of the above statements, further comprising: suggesting a lesson to the user based on the performance of the user.

Statement 9: The method of any of the above statements, wherein the feedback device provides the feedback while the user continues the performance.

Statement 10: The method of any of the above statements, wherein the feedback comprises at least one of audio feedback, haptic feedback, and near-eye display feedback.

Statement 11: The method of any of the above statements, wherein the processing of the data to evaluate the performance of the user further comprises: determining, using the processed data, a category of a surface on which the user is conducting the performance Statement 12: The method of any of the above statements, wherein the data is recorded by the at least one sensor as the user is skiing, wherein each ski turn is detected using a peak detection on the processed data, and wherein the processed data is averaged across each ski turn to form a new performance metric for use in evaluating of the performance.

Statement 13: The method of any of the above statements, wherein the feedback device displays to the user a traced travel path of the user with changes in color describing changes in the processed data Statement 14: The method of any of the above statements, wherein the feedback device is one of a smartphone and a tablet.

Statement 15: The method of any of the above statements, wherein the at least one sensor measures capacitance, the capacitance varying as the user applies pressure within the footwear.

Statement 16: A system comprising: capacitance sensor in footwear of a user, the capacitance sensor being located between a foot cavity of the footwear and a sole of the footwear; a processor; and a computer-readable storage medium having instructions stored which, when executed by the processor, perform operations comprising: identifying, at the capacitance sensor, pressure related data associated with a performance of the user; and transmitting the pressure related data to a feedback device.

Statement 17: The system of Statement 16, wherein the footwear comprises one of a snow ski boot and a snowboard boot.

Statement 18: The system of Statement 16, wherein the footwear of the user comprises one of a water skiing boot, a wakeboarding boot, a tennis shoe, an ice skate, a golf shoe, a rowing shoe, a horse riding boot, and a cycling shoe.

Statement 19: The system of any of Statements 16 to 18, wherein the transmitting of the pressure related data occurs through one of a Bluetooth transmission, a Wi-Fi transmission, and radio frequency transmission.

Statement 20: The system of any of Statements 16 to 19, wherein the capacitance sensor comprises: an accelerometer; a magnetometer; and a gyroscope.

Statement 21: The system of any of Statements 16 to 20, wherein the sensor is coupled via a cable to the processor, and wherein the transmitting of the pressure related data occurs using a Radio Frequency signal.

Statement 22: The system of any of Statements 16 to 21, wherein the sensor identifies the pressure related data by measuring a change in capacitance between constituent components of the sensor.

Statement 23: The system of any of Statements 16 to 22, further comprising: a feedback device; and the computer-readable storage medium having additional instructions stored which, when executed by the processor, cause the processor to perform operations comprising: receiving, in response to the transmitting of the pressure related data, feedback data from the data processing device; providing, during a continuation of the performance, feedback via the feedback device to the user regarding the performance based on the feedback data, wherein the feedback comprises at least one of audio feedback, haptic feedback, and near-eye display feedback.

Statement 24: The system of any of Statements 16 to 23, wherein the sensor comprises: a flexible printed circuit; an elastomeric layer; and a conductive layer.

Statement 25: The system of any of Statements 16 to 24, further comprising: a data collection unit; and the computer-readable storage medium having additional instructions stored which, when executed by the processor, cause the processor to perform operations comprising: storing the pressure related data in a data collection unit prior to the transmitting of the pressure related data.

Statement 26: The system of any of Statements 16 to 25, wherein the data collection unit stores performance metrics from a previous performance.

Statement 27: A computer-readable storage device having instructions stored which, when executed by a computing device, cause the computing device to perform operations comprising: receiving data at the computing device, wherein the data is received from at least one sensor in footwear of a user, the at least one sensor being located between a foot a foot cavity of the footwear and a sole of the footwear; processing the data to evaluate a performance of the user, to yield processed data; and transmitting the processed data to a feedback device, wherein the feedback device provides feedback to the user regarding the performance of the user using the processed data.

Statement 28: A method comprising: receiving data at a server, wherein the data is received from at least one sensor in footwear of a user, the at least one sensor being located between a foot of the user and a sole of the footwear; calculating, using the data, a weight distribution of the user over the footwear; evaluating a performance of the user using the center of mass, to yield processed data; and transmitting the processed data to a feedback device, wherein the feedback device provides feedback to the user regarding the performance of the user using the processed data.

Statement 27: The method of Statement 26, wherein the footwear of the user comprises a snow ski boot.

Statement 28. The method of Statements 26 or 27, wherein the data is recorded by the at least one sensor as the user is skiing, wherein each ski turn is detected, and wherein the processed data is averaged across each ski turn to form a new performance metric for use in the evaluating of the performance.

Statement 29: The method of any of Statements 26 to 28, wherein the processed data is displayed by the feedback device and shows a traced travel path of the user with changes in color describing changes in the processed data.

Statement 30: A system comprising: a sensor in a band which wraps around a leg of a user, the sensor being located between the leg and a snow ski boot; a processor; and a computer-readable storage medium having instructions stored which, when executed by the processor, perform operations comprising: identifying, at the sensor, pressure data.

Statement 31: The system of Statement 30, wherein the sensor is a capacitive sensor which measures capacitance, the capacitance being modified as the user applies pressure within the snow ski boot.

We claim:

1. A method comprising:
   measuring data using at least one sensor, wherein the data is received from the at least one sensor in footwear of a user, the at least one sensor being located in an insole between a foot of the user and a sole of the footwear;
   processing the data using a processing unit located on the exterior of the footwear to evaluate a performance of the user, to yield processed data,
   wherein the processing unit is separate from the insole; and
   transmitting the processed data to a feedback device, wherein the feedback device provides feedback to the user regarding the performance of the user for a plurality of ski turns;
   wherein for each ski turn processing the data comprises:
      detecting a ski turn using a peak detection; and
      determining a performance metric relating to the ski turn; and
   wherein for each ski turn transmitting the processed data comprises transmitting the performance metric to the user once the user completes the ski turn.

2. The method of claim 1, wherein the footwear of the user comprises one of a ski boot, a snowboarding boot, a water skiing boot, a wakeboarding boot, an ice skate, a golf shoe, a rowing shoe, a horse riding boot, and a cycling shoe.

3. The method of claim 1, wherein the processing of the data to evaluate the performance of the user further comprises:
   identifying a pressure applied to the at least one sensor by a foot of the user;
   identifying a position and an orientation of the user; and
   comparing the pressure, the position, and the orientation to a best practice threshold.

4. The method of claim 1, wherein the processing of the data to evaluate the performance of the user further comprises:
   combining the processed data with a video of the performance of the user.

5. The method of claim 1, further comprising receiving second data from a second sensor associated with the user, wherein the second sensor is not associated with the footwear; and
   utilizing the second data during the processing of the data.

6. The method of claim 5, wherein the second sensor is embedded in one of a ski pole, a helmet, a snow glove, and a goggle.

7. The method of claim 1, further comprising:
   suggesting a lesson to the user based on the performance of the user.

8. The method of claim 1, wherein the feedback device provides the feedback while the user continues the performance.

9. The method of claim 1, wherein the processing of the data to evaluate the performance of the user further comprises:
   determining, using the processed data, a category of a surface on which the user is conducting the performance, and wherein determining the category comprises determining a type of material of a surface using a transform, in the form of a Fourier transform.

10. The method of claim 1, wherein the feedback comprises at least one of audio feedback, haptic feedback, and near-eye display feedback and/or wherein the feedback device displays to the user at least one of:
    a graphic of the each turn with changes in color describing changes in the processed data using the new performance metric; and
    a traced travel path of the user with changes in color describing changes in the processed data.

11. The method of claim 1, wherein the feedback device is one of a smartphone and a tablet.

12. The method of claim 1, wherein the at least one sensor measures capacitance, the capacitance varying as the user applies pressure within the footwear.

13. A system comprising:
a capacitance sensor in footwear of a user, the capacitance sensor being located in an insole between a foot of a user and a sole of the footwear;
a processor located on the exterior of the footwear and separate from the insole; and
a computer-readable storage medium having instructions stored which, when executed by the processor, perform operations comprising:
processing pressure related data from the capacitance sensor associated with a performance of the user for a plurality of ski turns; and
transmitting the pressure related data to a data processing device;
wherein for each ski turn processing the data comprises:
detecting a ski turn using a peak detection; and
determining a performance metric relating to the ski turn; and
wherein for each ski turn transmitting the processed data comprises transmitting the performance metric to the user after the user completes the ski turn.

14. The system of claim 13, further comprising:
an accelerometer;
a magnetometer; and
a gyroscope.

15. The system of claim 14, wherein the capacitance sensor is coupled via a cable to the processor, and wherein the transmitting of the pressure related data occurs using a Radio Frequency signal.

16. The system of claim 15, further comprising:
a feedback device; and
the computer-readable storage medium having additional instructions stored which, when executed by the processor, cause the processor to perform operations comprising:
receiving, in response to the transmitting of the pressure related data, feedback data from the data processing device; and
providing, during a continuation of the performance, feedback via the feedback device to the user regarding the performance based on the feedback data, wherein the feedback comprises at least one of audio feedback, haptic feedback, and near-eye display feedback.

17. The method of claim 1, wherein the processing unit is located on the back of the footwear.

18. The method of claim 1, wherein the insole and the processing unit are connected using a cable, wherein the cable has a non-uniform friction.

19. The method of claim 1, wherein determining that a turn has occurred comprises evaluating at least one of a yaw, a roll, and a pitch of the user's feet and/or wherein the turn is detected using a peak in the data.

20. The method of claim 1, further comprising determining the end of the turn.

21. The method of claim 1, wherein the performance metric comprises a transition point.

22. A method comprising:
measuring data using at least one sensor, wherein the data is received from the at least one sensor in footwear of a user, the at least one sensor being located in an insole between a foot of the user and a sole of the footwear;
processing the data using a processing unit located on the exterior of the footwear to evaluate a performance of the user, to yield processed data, wherein the processing unit is separate from the insole; and
transmitting the processed data to a feedback device, wherein the feedback device provides feedback to the user regarding the performance of the user for a plurality of ski turns;
wherein for each ski turn processing the data comprises:
detecting a ski turn using a peak detection; and
determining a transition point relating to the ski turn; and
wherein for each ski turn transmitting the processed data comprises transmitting the transition point to the user once the user completes the ski turn.

* * * * *